(12) United States Patent
Hare et al.

(10) Patent No.: US 11,669,883 B2
(45) Date of Patent: Jun. 6, 2023

(54) SECURITY MODEL AND INTERFACE FOR DIGITAL PURCHASES ON A WEARABLE DEVICE

(71) Applicant: Apple Inc., Cupertino, CA (US)

(72) Inventors: Peter J. Hare, San Francisco, CA (US); Dana J. DuBois, San Francisco, CA (US); Eric O. Carlson, Mountain View, CA (US); Lori Hylan-Cho, Cupertino, CA (US); Keith P. Kowalczykowski, San Francisco, CA (US); Matthew Sibson, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 430 days.

(21) Appl. No.: 16/882,128

(22) Filed: May 22, 2020

(65) Prior Publication Data

US 2020/0380585 A1     Dec. 3, 2020

Related U.S. Application Data

(60) Provisional application No. 62/856,030, filed on Jun. 1, 2019.

(51) Int. Cl.
*G06Q 30/06* (2023.01)
*G06Q 20/32* (2012.01)
(Continued)

(52) U.S. Cl.
CPC ..... *G06Q 30/0633* (2013.01); *G06Q 20/3227* (2013.01); *G06Q 30/0601* (2013.01); *G16H 40/67* (2018.01)

(58) Field of Classification Search
None
See application file for complete search history.

(56) References Cited

U.S. PATENT DOCUMENTS 6,839,841 B1 * 1/2005 Medvinsky ........... H04L 63/062
                                                                713/168
7,774,708 B2    8/2010 Bell et al.
(Continued)

FOREIGN PATENT DOCUMENTS

EP           3128392 A1 *  2/2017  ........... A61B 5/6824
WO      2020227133 A1     11/2020

OTHER PUBLICATIONS

Weckler, A., "Samsung hoping hi-tech watches make market tick," Irish Independent [Dublin] Feb. 24, 2014: 28. (Year: 2014).*

(Continued)

*Primary Examiner* — Nicholas D Rosen

(74) *Attorney, Agent, or Firm* — Kilpatrick Townsend & Stockton LLP

(57) ABSTRACT

Embodiments described herein provide a security model and interface for wearable device digital purchases that can be made without the assistance of a companion device. The satellite device can be configured to be used as a primary device, without reliance upon a paired device. A provisioning process may be implemented to generate and validate one or more tokens to authenticate the wearable device and a set of cryptographic keys can be generated. Subsequently, the token(s) and cryptographic keys may be used to enable a user of the wearable device to make purchases from a digital shopping store without support from an associated companion electronic device.

20 Claims, 15 Drawing Sheets

(51) Int. Cl.
*G16H 40/67* (2018.01)
*G06Q 30/0601* (2023.01)

(56) References Cited

U.S. PATENT DOCUMENTS

| | | | |
|---|---|---|---|
| 8,161,411 B2 | 4/2012 | Robbin et al. | |
| 9,124,637 B2 | 9/2015 | Brouwer et al. | |
| 9,173,115 B2 | 10/2015 | Sundareswaran et al. | |
| 9,326,091 B2 | 4/2016 | Donnellan et al. | |
| 9,471,697 B2 | 10/2016 | Lortz et al. | |
| 9,473,509 B2 | 10/2016 | Arsanjani et al. | |
| 9,530,027 B2* | 12/2016 | Shahidzadeh | H04L 9/3242 |
| 9,554,274 B1* | 1/2017 | Castinado | H04W 4/023 |
| 9,612,862 B2 | 4/2017 | Faaborg et al. | |
| 9,665,357 B2 | 5/2017 | Nigam | |
| 9,763,097 B2* | 9/2017 | Robinson | H04W 12/08 |
| 9,830,170 B2 | 11/2017 | Mun et al. | |
| 9,838,526 B2 | 12/2017 | Donley et al. | |
| 9,842,062 B2 | 12/2017 | Ford et al. | |
| 9,955,286 B2 | 4/2018 | Segal | |
| 10,078,748 B2* | 9/2018 | Mehta | G06F 21/45 |
| 10,095,500 B2 | 10/2018 | Pollack et al. | |
| 10,122,723 B1 | 11/2018 | Chang et al. | |
| 10,811,140 B2* | 10/2020 | Toumazou | G06K 19/06028 |
| 10,867,606 B2* | 12/2020 | Li | G06K 19/06037 |
| 10,885,510 B2* | 1/2021 | Yarbrough | G06Q 20/322 |
| 11,062,807 B1 | 7/2021 | Ross et al. | |
| 11,176,539 B2* | 11/2021 | Mohamed | G06Q 20/4014 |
| 11,528,271 B2 | 12/2022 | Belov et al. | |
| 2002/0049806 A1 | 4/2002 | Gatz et al. | |
| 2012/0210246 A1* | 8/2012 | Bylehn | H04L 63/102 |
| | | | 715/748 |
| 2013/0086232 A1 | 4/2013 | Hwang et al. | |
| 2014/0337621 A1* | 11/2014 | Nakhimov | H04W 12/068 |
| | | | 713/168 |
| 2015/0242837 A1* | 8/2015 | Yarbrough | G06Q 20/327 |
| | | | 705/44 |
| 2015/0264722 A1 | 9/2015 | Cheng et al. | |
| 2015/0348032 A1 | 12/2015 | Ioveva et al. | |
| 2016/0062572 A1 | 3/2016 | Yang et al. | |
| 2016/0070439 A1* | 3/2016 | Bostick | G06F 3/0304 |
| | | | 715/728 |
| 2016/0078571 A1* | 3/2016 | Singh | G06Q 30/0633 |
| | | | 705/14.66 |
| 2016/0224810 A1* | 8/2016 | Shahidzadeh | H04W 12/126 |
| 2016/0262094 A1 | 9/2016 | Khay-Ibbat et al. | |
| 2016/0337863 A1* | 11/2016 | Robinson | H04W 4/021 |
| 2017/0095803 A1 | 4/2017 | Nazarpoor et al. | |
| 2017/0140146 A1* | 5/2017 | Mehta | H04L 9/3234 |
| 2017/0278365 A1 | 9/2017 | Madar et al. | |
| 2017/0357967 A1* | 12/2017 | Sykora | H04L 63/0861 |
| 2018/0069871 A1 | 3/2018 | Fasoli et al. | |
| 2018/0165936 A1 | 6/2018 | Smith et al. | |
| 2018/0176968 A1 | 6/2018 | Reunamaki et al. | |
| 2018/0342176 A1* | 11/2018 | Califorrniaa | G09B 21/004 |
| 2019/0050218 A1 | 2/2019 | Giatilis et al. | |
| 2019/0138145 A1* | 5/2019 | Brisimitzakis | G04G 17/08 |
| 2019/0279637 A1* | 9/2019 | Li | G06F 3/167 |
| 2019/0325495 A1* | 10/2019 | Stark | G06Q 30/0613 |
| 2020/0151707 A1* | 5/2020 | Mohamed | G06Q 20/409 |
| 2020/0151827 A1 | 5/2020 | Carver et al. | |
| 2020/0303076 A1* | 9/2020 | Toumazou | G06F 1/163 |
| 2020/0359204 A1 | 11/2020 | Hawkins et al. | |

OTHER PUBLICATIONS

Anon., "C Spire Launches Samsung Galaxy S(R) on Its Network," Business Wire [New York] May 20, 2014. (Year: 2014).*

Anon., "Armani Exchange Launches First Ever Connected Wearables Line With New Hybrid Smartwatch Collection: Smartwatches Announced at 2017 Consumer Electronics Show," PR Newswire [New York] Jan. 4, 2017. (Year: 2017).*

Owens, "Using a Cellular Apple Watch as Your Kid's Cell Phone", Available Online at: https://geekdad.com/2018/07/using-a-cellular-apple-watch-as-your-kids-cell-phone/, Jul. 19, 2018, 27 pages.

* cited by examiner

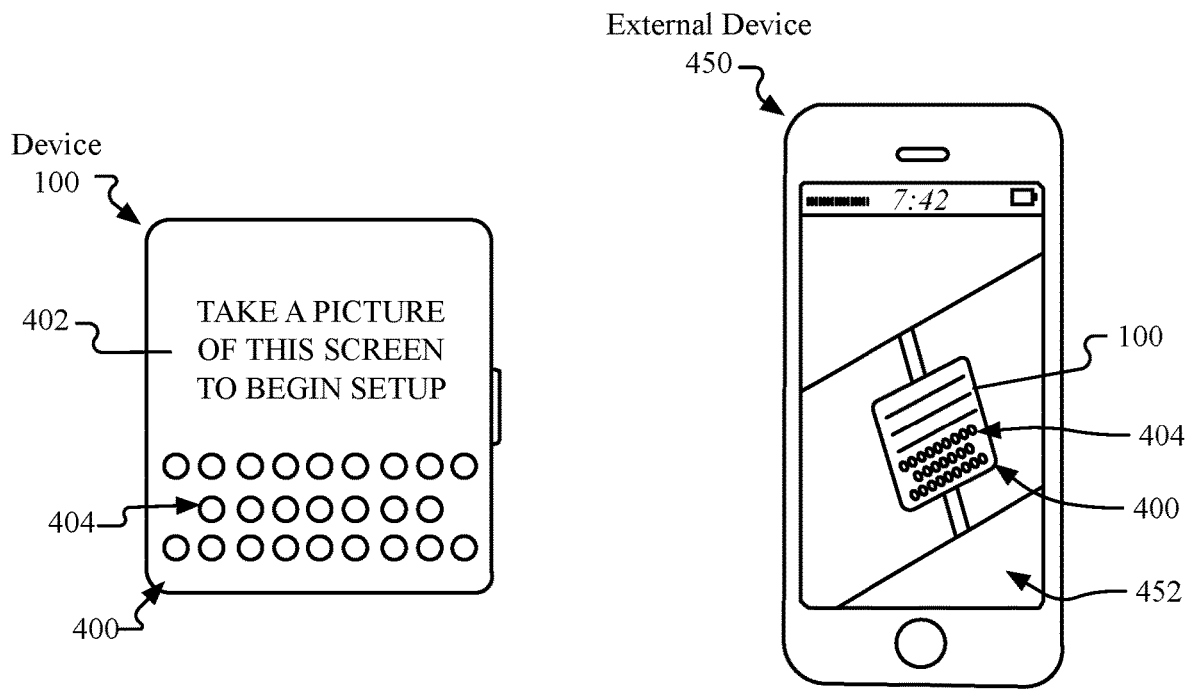
*FIG. 4A*  *FIG. 4B*
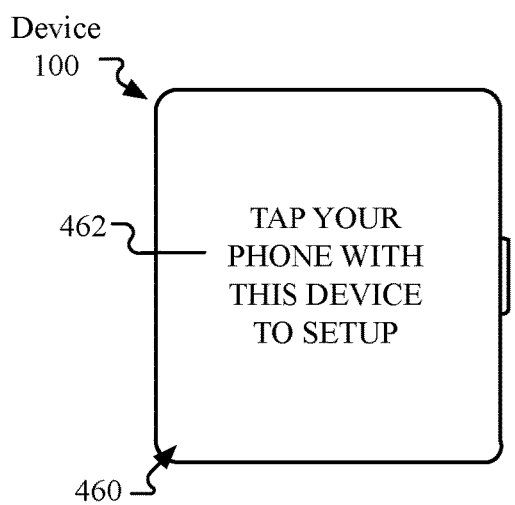
*FIG. 4C*

US 11,669,883 B2

SECURITY MODEL AND INTERFACE FOR DIGITAL PURCHASES ON A WEARABLE DEVICE

CROSS-REFERENCE

This application claims priority to U.S. Provisional Application Ser. No. 62/856,030, filed on Jun. 1, 2019, the entire contents of which is hereby incorporated herein by reference.

BACKGROUND OF THE DISCLOSURE

In addition to keeping time, users may desire wearable electronic devices to be able to perform a variety of other operations including running software applications. A user may wish to access different types of information, such as various aspects related to keeping time, or different application data points, in different contexts. Generally, wearable electronic devices are associated or paired with a companion device, through which many operational details of the wearable device may be configured.

SUMMARY OF THE DESCRIPTION

Embodiments described herein provide for a security model and interface for wearable device digital purposes. Embodiments enable a "thin" wearable device (e.g., a smart watch, smart glasses, bracelet, or the like) to be configured to be used as a primary device for making purchases of digital content, without reliance upon a companion electronic device, e.g., smartphone, computer, or the like.

One embodiment provides for a wearable device comprising a wireless network interface, a touch-sensitive display, a memory device to store instructions, and one or more processors to execute the instructions. The instructions cause the one or more processors to present, via the touch-sensitive display, a user interface to enable the wearable device to establish a communication connection with a server of a cloud service provider via the wireless network interface and transact a digital purchase from the server without assistance from a companion device.

One embodiment provides a non-transitory machine-readable medium storing instruction which, when executed by one or more processors of a wearable electronic device, cause the one or more processors to perform operations comprising presenting a request for a passcode used to unlock the wearable electronic device, receiving the passcode via the interface, using the passcode to unlock one or more keys that are securely stored on the wearable electronic device, establishing a communication connection with a server of a cloud service provider via a wireless network interface of the wearable device, and transacting a digital purchase from the server without assistance from a companion device, wherein the digital purchase is transacted at least in part using a signature generated with the one or more keys.

One embodiment provides for a data processing system on a wearable electronic device, the system comprising a wireless network interface, a touch-sensitive display, a memory device to store instructions, and one or more processors to execute the instructions. The instructions cause the one or more processors to present, via the touch-sensitive display, a user interface to enable the wearable device to present a request for a passcode used to unlock the wearable electronic device, receive the passcode via the interface, use the passcode to unlock one or more keys that are securely stored on the wearable electronic device, establish a communication connection with a server of a cloud service provider via the wireless network interface, and transact a digital purchase from the server without assistance from a companion device, wherein the digital purchase is transacted at least in part using a signature generated with the one or more keys.

Other features of the present embodiments will be apparent from the accompanying drawings and from the detailed description, which follows.

BRIEF DESCRIPTION OF THE DRAWINGS

Embodiments of the present invention are illustrated by way of example, and not limitation, in the figures of the accompanying drawings in which reference numbers are indicative of origin figure, like references may indicate similar elements, and in which:

FIG. 4A-4C show exemplary setup instruction screens for a wearable device;

DETAILED DESCRIPTION

Figure 1B:
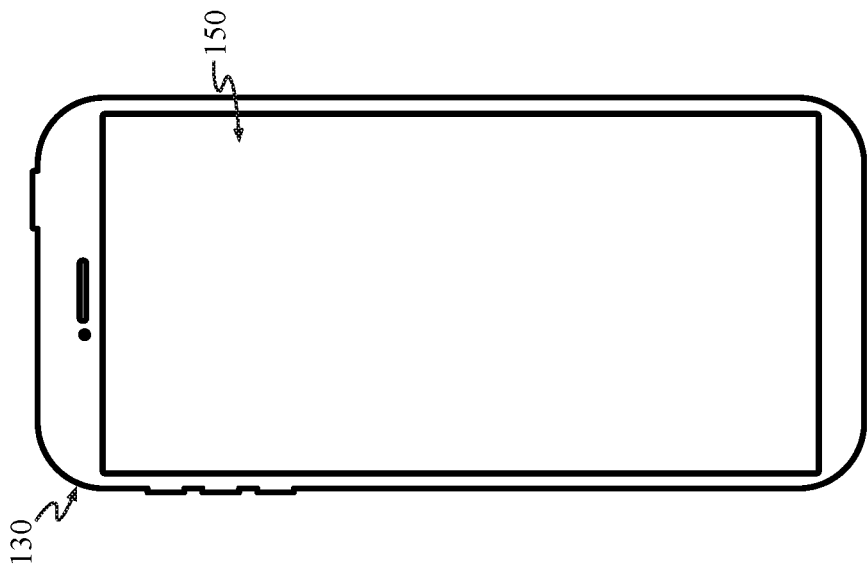
FIG. 1A-1B illustrates a wearable device and a companion mobile device, according to embodiments described herein.

While, wearable electronic devices are generally associated or paired with a companion device, embodiments described herein provide a wearable electronic device that can be operated without an associated companion device. More particularly, embodiments described herein provide a security model and interface for wearable device digital purchases that enables a wearable device to effect secure purchases from a digital shopping store without support from an associated companion electronic device. In this context, a companion device is an electronic device that is connected to, paired with, or associated with a wearable electronic device. The companion device may be in continuous or periodic communication with the wearable electronic device and can perform computing operations in concert with or on behalf of the wearable device. For example, a smartphone or tablet computing device may be a companion device to a wearable electronic device, such as, but not limited to, a smartwatch device.

The wearable electronic device can have a wireless network interface, a touch sensitive display, a memory to store instructions, and one or more processors capable to execute the instructions. When executed, the instructions cause the one or more processors to present, via the touch-sensitive display, a user interface to enable the wearable electronic device to establish a communication connection with a server of a cloud service provider via the wireless network interface and transact a digital purchase from the server without assistance from a companion electronic device.

During a provisioning process performed in conjunction with a companion device, a wearable electronic device can be assigned a passcode that is unique to the wearable device. The passcode may be provided to a cloud-based server which generates a token, sometimes referred to as a password equivalent token (PET), based on the passcode. The PET may be received in a media services daemon, which passes the PET to an authentication process. The authentication process may return a secure authentication token to the media services daemon, which passes the secure token and a public key generated by the wearable electronic device to an identification settings process. The identification settings process returns an identification token uniquely associated with the wearable electronic device, which is stored in association with a public-private key pair for the wearable electronic device in a secure memory location.

Subsequently, a user of the wearable electronic device may initiate a purchase request from a digital shopping facility. The received purchase request and the identification token associated with the wearable electronic device may be passed to an identification authentication process, which attempts to validate the identification token. If the identification token is validated, then the authentication process returns a biometric challenge to be signed by the media services daemon. The media sever initiates a request for the user to enter a passcode in the wearable electronic device, which is returned to the media services daemon with the public/private keys associated with the wearable electronic device. The media services daemon uses the passcode and the public-private key pair for the wearable device to generate a signed biometric challenge, which is passed with the purchase request to the identification authentication process. In response, the identification authentication process generates and approval for the purchase request, and the media services daemon completes the purchase request.

By contrast, if the identification token is not validated then the media services daemon initiates a process to require the wearable electronic device to be re-provisioned in cooperation with the companion device. When the re-provisioning process is complete the purchase request may be processed as described above.

Reference in the specification to "one embodiment" or "an embodiment" means that a feature, structure, or characteristic described in conjunction with the embodiment can be included in at least one embodiment of the invention. The appearances of the phrase "in one embodiment" in various places in the specification do not necessarily all refer to the same embodiment.

The processes depicted in the figures that follow may be performed by processing logic that comprises hardware (e.g. circuitry, dedicated logic, etc.), software (as instructions on a non-transitory machine-readable storage medium), or a combination of both hardware and software. Although the processes are described below in terms of some sequential operations, it should be appreciated that some of the operations described may be performed in a different order. Moreover, some operations may be performed in parallel rather than sequentially.

Exemplary Wearable and Companion Electronic Device

Figure 1A:
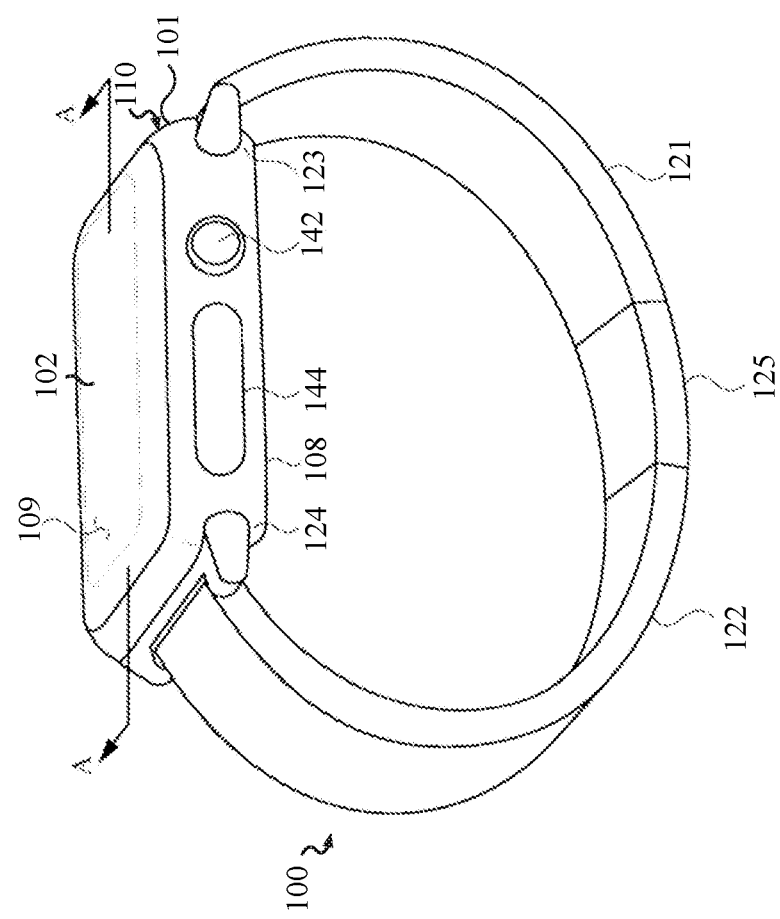

FIG. 1A-1B illustrates a wearable electronic device and a companion mobile electronic device, according to embodiments described herein. FIG. 1A illustrates a wearable electronic device in the form of a wristwatch device. FIG. 1B illustrates an exemplary mobile electronic device in the form of a smartphone device. Although specific examples are shown, embodiments described herein are applicable to additional electronic devices. For example, exemplary wearable electronic devices include various forms of time keeping devices, electronic or computerized glasses, sports related devices, pedometers, and or health and medical devices. Exemplary mobile electronic devices include tablet computers, navigation devices, and may also include laptop computers.

As shown in FIG. 1A, one embodiment provides a wearable electronic device 100 that includes a device body 110 that can be attached to a wrist of a user using a band assembly. The exterior surface of the device body 110 is defined, in part, by the exterior surface of a housing 101 and the exterior surface of a cover 109. The device body 110 is substantially rectangular with round or curved side portions, although other shapes and/or designs can be implemented. The outer surfaces of the cover 109 and the housing 101 coincide at a joint interface and cooperate to form a continuous contoured surface. The continuous contoured surface may have a constant radius and may be tangent to a flat middle portion of the cover 109 and/or a flat bottom portion of the housing 101. In some embodiments, the cover 109 has substantially the same shape as a flat bottom portion and at least a portion of the curved side portions of the housing 101. The housing 101 may be formed from a variety of materials, including, without limitation plastic, glass, ceramics, fiber composites, metal (e.g., stainless steel, aluminum, magnesium), other suitable materials, or a combination of these materials. Further, the housing 101 may include a surface treatment or coating, which may be formed from a variety of materials, including, without limitation aluminum, steel, gold, silver and other metals, metal alloys, ceramics, wood, plastics, glasses, and the like.

The illustrated wearable electronic device 100 may be referred to herein as a wearable device, a device, an electronic wristwatch, or an electronic watch. While these terms may be used with respect to certain embodiments, the functionality provided by the illustrated electronic wearable device 100 may be substantially greater than or vary with respect to many traditional electronic watches or timekeeping devices. For example, the techniques described herein are applicable to any wearable device. In addition to smart watch devices, a wearable device described herein can be or include GPS trackers, fitness trackers, glasses (e.g., virtual reality, mixed reality, and/or augmented reality head mounted displays), jewelry, shoes, clothes, or other wearable items, heart monitors, health sensors, glucose monitors, audio accessories (e.g., headphones or earphones) and other accessories that can worn by a user. Thus, even though the portions of the following description use smartwatches as example wearable devices, embodiments provide techniques that can apply to other types of accessories The wearable electronic device 100 includes a display 102 that is disposed at least partially within an opening or cavity defined within a top portion of the housing 101 of the device body 110. The display may be formed from a liquid crystal display (LCD), organic light emitting diode (OLED) display, organic electroluminescence (OEL) display, or other type of display device. The display 102 may be used to present visual information to the user and may be operated in accordance with one or more display modes or the software applications being executed on the device 100. By way of example, the display may be configured to present the current time and date similar to a traditional watch or timepiece. The display may also present a variety of other visual information that may correspond to or be produced using one of the other modules in the wearable electronic device 100. For example, the display 102 may be configured to display one of a variety of notification messages, which can be generated based on data received from the one or more sensors, the wireless communication system, or other subsystem of the wearable electronic device 100. The display 102 may also be configured to present visual information or data that is based on the output of one or more sensor outputs. The display 102 can also provide status or information related to a wireless charging process or battery power. The display 102 can also present visual output or information related to media being produced using a speaker or acoustic module of the wearable electronic device 100. Accordingly, a variety of other types of visual output or information may be presented using the display.

In the current example, the display 102 includes or is integrated with a cover 109 that helps to protect the display from physical impact or scratches. In the field of wearable devices, the cover 109 may also be referred to generically as a crystal or cover glass, regardless of the material that is used to form the cover 109. In some cases, the cover 109 is formed from a sheet or block of sapphire material. Sapphire may provide superior optical and surface hardness properties as compared to other materials. In some cases, the sapphire material has a hardness of approximately 9 on the Mohs scale. In alternative embodiments, the cover 109 is formed from a glass, polycarbonate, or other optically transparent material. The cover 109 may also be coated with one or more optical or mechanical enhancing materials or surface treatments. For example, interior and/or exterior surfaces of the cover 109 may be coated with an anti-reflective (AR), oleophobic or other coating to enhance the visible or functional properties of the display. In some cases, the cover 109 may be configured to cooperate with an antenna used to facilitate wireless communication with an external device.

The cover 109 is formed from a transparent or semi-transparent material and, when assembled has an external surface and an internal surface. The cover 109 is disposed above the display and encloses a cavity or opening formed in the top portion of the housing 101. In some embodiments, the external surface of the cover 109 cooperates with the external surface of the housing to form a substantially continuous external peripheral surface of the electronic device. The external surface of the cover 109 has a flat middle portion at the center of the cover, which extends outwardly. The cover 109 can also include a curved edge portion that emanates from and surrounds the flat middle portion and extends outwardly to an edge at the side of the cover 109. In some embodiments, the cover 109 also includes an opaque mask disposed relative to the internal surface of the transparent cover. The opaque mask may correspond to or otherwise define the viewable area of the display 102. The mask may have an outer boundary that is located proximate the edge of the side of the cover 109 and has an inner boundary located within the curved edge portion of the cover 109.

In some instances, the cover 109 is disposed relative to a touch sensor, which may be integrated with the display 102 or other element of the wearable electronic device 100. The touch sensor can be formed from one or more capacitive sensor electrodes or nodes that are configured to detect the presence and/or location of an object or the user's finger that is touching or nearly touching the surface of the display. In some cases, the touch sensor includes an array of sensing nodes formed in accordance with a mutual capacitance sensing scheme. Alternatively or additionally, the touch sensor may include one or more self-capacitive nodes or electrodes that are configured to detect a discharge of electrical current or charge when an object, such as a user's finger, contacts or nearly contacts a surface of the housing 101 or other surface of the wearable electronic device 100. Other types of electronically sensing nodes, including resistive, inductive, or the like, may also be integrated into a surface of the wearable electronic device 100.

In some embodiments, the wearable electronic device 100 may also include a force sensor. The force sensor may be disposed relative to the display 102 or integrated with other elements of the wearable electronic device 100. In some cases, the force sensor includes one or more force sensing structures or force-sensing nodes for detecting and measuring the magnitude of a force or pressure due to a touch on a surface of the wearable electronic device 100. The force sensor may be formed from or implement one or more types of sensor configurations. For example, capacitive and/or strain based sensor configurations may be used alone or in combination to detect and measure the magnitude of a force or pressure due to a touch. As described in more detail below, a capacitive force sensor may be configured to detect the magnitude of a touch based on the displacement of a surface or element on the device. Additionally or alternatively, a strain-based force sensor may be configured to detect the magnitude of a touch based on the deflection.

As discussed above, the display, the touch sensor, and force sensor may be disposed within the housing 101. In this example, one or more buttons 144 and a crown 142 used to receive user input may also be disposed within or relative to the housing 101. Other types of user input, including for example, one or more dials, slides, or similar user input devices or mechanisms may also be disposed within or relative to the housing 101. The housing 101 can include various features for attaching and mounting the subassemblies and modules of the device 100. In particular, the housing 101 may have one or more openings for receiving the cover 109, the display, the force sensor, or other components. The housing 101 may also include one or more holes or openings for receiving the button 144 and crown 142 that are located around the perimeter of the wearable electronic device 100. In some embodiments, the housing 101 also includes internal features, such as bosses and threaded portions, that can be used to attach modules or components within the housing 101.

The wearable electronic device 100 may also include an ambient light sensor (ALS) that is configured to detect and measure changes in ambient lighting conditions. The ALS may include a photodiode and one or more optical elements or lenses for collecting light. An ALS may be located on an external facing surface that is less likely to be blocked when the device is worn or in use. The ALS may be used to adjust settings, including screen brightness and other visual output depending on the overall lighting conditions.

The housing 101 may also include one or more motion-sensing elements or devices for detecting motion of the wearable electronic device 100. For example, the wearable electronic device 100 may include one or more accelerometers that are configured to sense acceleration or changes in motion. Additionally or alternatively, the wearable electronic device 100 may include one or more gyroscopic sensors that are configured to detect changes in direction. In some cases, the one or more gyroscopic sensors may include a spinning mass that can be used to detect changes in angular velocity. Multiple motion-sensing elements may be used to detect motion along multiple directions or axes. The motion sensors may also be used to identify motion gestures. For example, the motion sensors can be used to detect an arm raise or the position of a user's body (within a predetermined confidence level of certainty). The one or more motion-sensing elements may be used to determine an orientation of the device relative to a known or fixed datum. For example, the device may include a compass and/or global positioning system (GPS) that can be used to identify an absolute position. The one or more motion sensing elements may then measure deviation or movement with respect to the absolute position to track movement of the device or the user wearing the device. In some implementations, the one or more motion-sensing elements are used to detect gross movement of the device or user. The gross movement may be used as a pedometer or activity meter, which may be tracked over time and used to calculate a health metric or other health-related information.

The housing 101 may also include one or more openings or orifices coupled to an acoustic module or speaker, which may include a speaker and/or a microphone subassembly. Although the housing 101 may include one or more openings or orifices, the housing 101 may still be substantially waterproof/water resistant and may be substantially impermeable to liquids. For example, the opening or orifice in the housing or enclosure may include a membrane or mesh that is substantially impermeable to liquid ingress. Additionally or alternatively, the geometry of the opening or orifice and other internal features of the housing 101 may be configured to reduce or impede the ingress of liquid or moisture into the device 100. In one example, the opening is formed from one or more orifices that are offset with respect to an internal acoustic chamber or cavity, which may prevent a direct path from the outside of the housing 101 into the acoustic module.

The wearable electronic device 100 includes a device body 110 that may be attached to a user's wrist using a band. In the present example, the band can include a first band strap 121 attached to a first receiving feature 123 and a second band strap 122 attached to a second receiving feature 124. In some embodiments, the first and second band straps 121, 122 include a lug feature that is configured to attach to the first and second receiving features 123, 124, respectively. The free ends of the band straps 121, 122 may be connected with a clasp 125.

The band straps 121, 122 are formed from a flexible or compliant material that may be specially configured for a particular application. The band straps 121, 122 may be formed from a variety of materials, including, for example, leather, woven textiles, or metallic mesh materials. The material and construction of the band straps 121, 122 may depend on the application. For example, the band straps 121, 122 may be formed from a woven textile material configured for exposure to impact and moisture typically associated with outdoor activities. In another example, the band straps 121, 122 may be formed from a metallic mesh material that may be configured to have a fine finish and construction that may be more appropriate for professional or social activities.

Similarly, the clasp 125 may be configured for a particular application or to work with a particular style of band. For example, if the band straps 121, 122 are formed from a metallic mesh material, the clasp 125 may include a magnetic clasp mechanism. In the present example, the device 100 is configured to be attached to the wrist of a user. However, in alternative embodiments, the device may be configured to be attached to the arm, leg or other body part of the user.

The housing 101 includes one or more features for attaching the band straps 121, 122. In the present example, the housing 101 includes a first receiving feature 123 and a second receiving feature 124 for attaching the first band strap 121 and the second band strap 122, respectively. In this example, the band straps 121, 122 include a lug portion that is adapted to mechanically engage with the receiving features 123, 124. The first receiving feature 123 and second receiving feature 124 may be integrally formed into the housing 101. In alternative embodiments, the receiving features may be formed from separate parts and may be attached to the housing 101 during manufacturing. In some embodiments, the receiving features 123, 124 may be configured to release the band straps 121, 122 from the device body 110 (e.g., the housing 101). For example, one or both of the receiving features 123, 124 may include a button or slide, which may be actuated by the user to release a corresponding band strap 121 and 122. One advantage of a releasable lug is that the user can swap between a variety of bands that may be specially configured for a particular use scenario. For example, some bands may be specially configured for sport or athletic activities and other bands may be configured for more formal or professional activities.

The wearable electronic device 100 may also include a rear cover 108 located on the rear-facing surface of the housing 101 of the device body 110. The rear cover 108 may improve the strength and/or scratch resistance of the surface of the wearable electronic device 100. For example, in some embodiments, the rear cover 108 may be formed from a sapphire sheet, zirconia, or alumina material having superior scratch resistance and surface finish qualities. In some cases, the sapphire material has a hardness greater than 1 on the Mohs scale. In some cases, the sapphire material has a hardness of approximately 9 on the Mohs scale. Due to the superior strength of the sapphire material, a cover glass formed from a sapphire sheet may be very thin. For example, the thickness of a sapphire cover sheet may be less 300 microns thick. In some cases, the thickness of a sapphire cover sheet may be less than 100 microns thick. In some cases, the thickness of a sapphire cover sheet may be less than 50 microns thick. In some embodiments, the rear cover 108 is contoured in shape. For example, the rear cover 108 may have a convex curved surface.

FIG. 1B illustrates a mobile electronic device 130 which may be a companion device of the wearable electronic device 100 of FIG. 1A. The illustrated mobile electronic device 130 includes a display 150 for providing an operating system or application graphical interface. In one embodiment the display 150 is a multi-function touchscreen display configured to accept touch or electronic pen input from a user. The mobile electronic device 130 can include one or more processing units, one or more network or other communications interfaces, memory, and one or more communication buses for interconnecting these components. The mobile electronic device 130 can execute an operating system that facilitates the execution of applications within memory of the mobile electronic device 130. Application programs may include phone programs, e-mail programs, personal information management (PIM) programs, word processing programs, spreadsheet programs, Internet browser programs, messaging programs, and the like. One or more of the application programs can work on concert with application programs executing on the wearable electronic device 100. For example, launching an application program on the mobile electronic device 130 or interacting with the application program via the display 150 can launch an application or cause an action to be performed on the wearable electronic device 100. In one embodiment, interacting with an application on the mobile electronic device 130 can cause an associated application on the wearable electronic device 100 to become a front-most application. In embodiments described herein, the front-most application executing on the wearable electronic device 100 can be granted enhanced execution capabilities, even when the wearable electronic device 100 is in a lower-power or screen-off state.

Figure 2A:
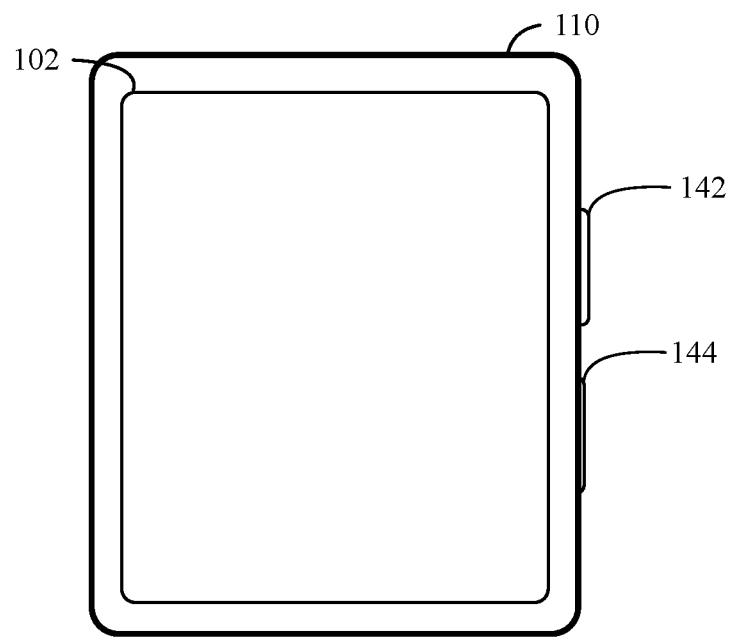
FIG. 2A-2B illustrate components of a wearable device, according to an embodiment.
Figure 2B:
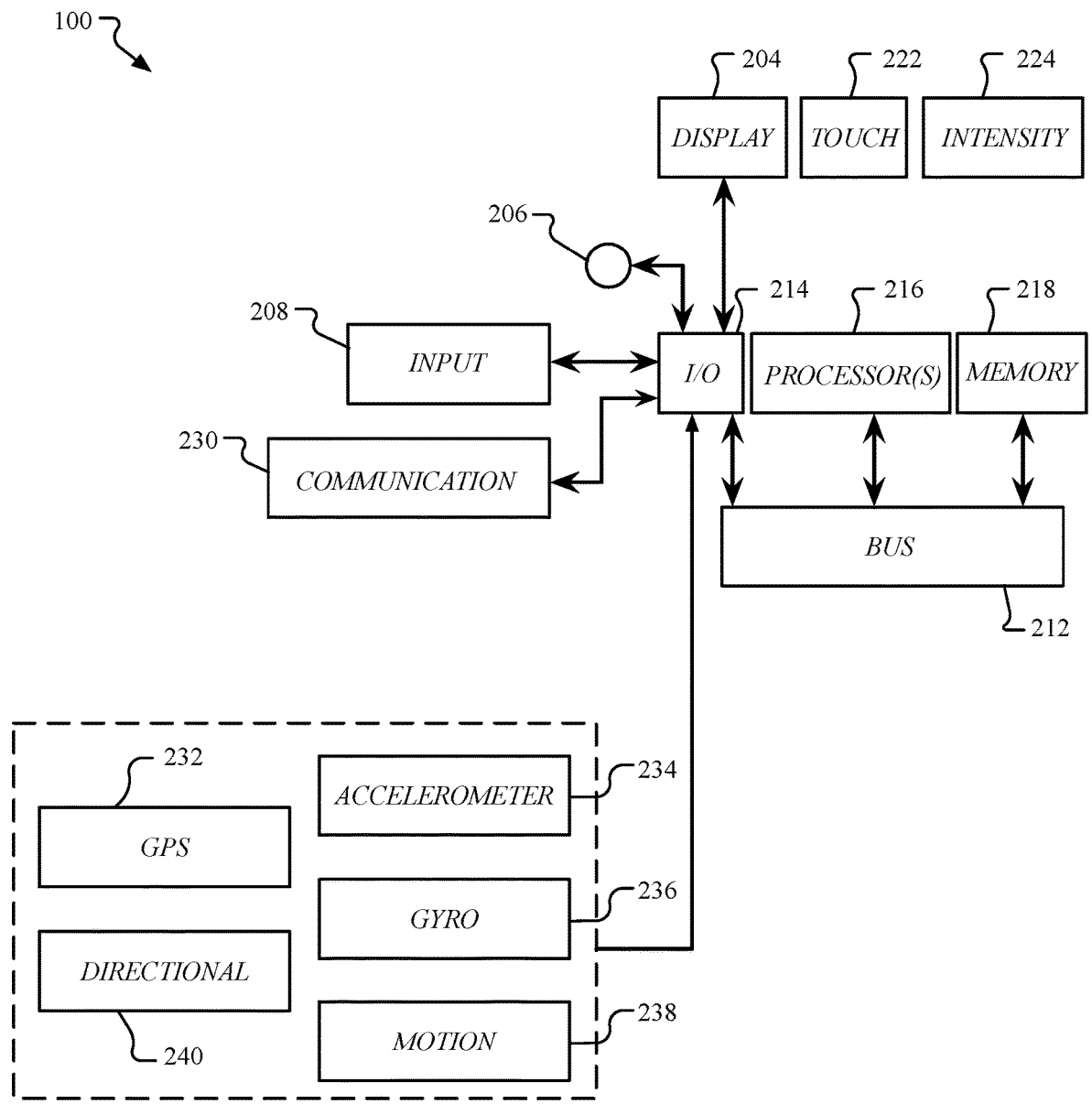

FIG. 2A-2B illustrate components of a wearable electronic device, according to an embodiment. FIG. 2A illustrates an external view of a wearable electronic device 100. FIG. 2B depicts internal components of the wearable electronic device 100.

As shown in FIG. 2A, device 100 includes body 110. In some embodiments, device 100 can include some or all of the features described with respect to device 100 of FIG. 1A. In some embodiments, device 100 has touch-sensitive display screen (e.g., touchscreen 102). Alternatively, or in addition to touchscreen 102, device 100 has a display and a touch-sensitive surface. In some embodiments, touchscreen 102 (or the touch-sensitive surface) may have one or more intensity sensors for detecting intensity of contacts (e.g., touches) being applied. The one or more intensity sensors of touchscreen 102 (or the touch-sensitive surface) can provide output data that represents the intensity of touches. The user interface of device 100 can respond to touches based on their intensity, meaning that touches of different intensities can invoke different user interface operations on device 100.

In some embodiments, device 100 has one or more input mechanisms, which may be physical input mechanisms. Examples of physical input mechanisms include push buttons and rotatable mechanisms, such as but not limited to the crown 142 and one or more buttons 144. In some embodiments, device 100 has one or more attachment mechanisms. Such attachment mechanisms, if included, can permit attachment of device 100 with, for example, hats, eyewear, earrings, necklaces, shirts, jackets, bracelets, watch straps, chains, trousers, belts, shoes, purses, backpacks, and so forth. These attachment mechanisms may permit device 100 to be worn by a user.

As shown in FIG. 2B device 100 has bus 212 that operatively couples I/O section 214 with one or more computer processors 216 and memory 218. The one or more processors 216 can include a low power system processor or processor core and a higher-powered application processor or processor core. The one or more computer processors 216 can also include a secure processor, such as but not limited to a secure enclave processor (SEP). The one or more computer processors 216 and I/O section 214 can be connected to a touchscreen display 204, which can have touch-sensitive component 222 and, optionally, touch-intensity sensitive component 224. In addition, I/O section 214 can be connected with communication unit 230 for receiving application and operating system data, using Bluetooth, near field communication (NFC), cellular, and/or other wireless communication techniques.

Device 100 can include one or more input mechanisms 206 and/or 208, such as but not limited to a rotatable input device (e.g., crown 142) or a depressible and rotatable input device (e.g., buttons 144). Additional input mechanisms 208 can include a microphone, in some examples. Device 100 can include various sensors, such as GPS sensor 232, accelerometer 234, directional sensor 240 (e.g., compass), gyroscope 236, motion sensor 238, and/or a combination thereof, all of which can be operatively connected to I/O section 214.

Memory 218 of wearable electronic device 100 can be a non-transitory computer-readable storage medium, for storing computer-executable instructions, which, when executed by one or more computer processors 216, for example, can cause the computer processors to perform the techniques described herein. The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer-readable storage medium" can be any medium that can tangibly contain or store computer-executable instructions for use by or in connection with the instruction execution system, apparatus, or device. Device 100 is not limited to the components and configuration of FIG. 2B but can include other or additional components in multiple configurations.

Figure 2C:
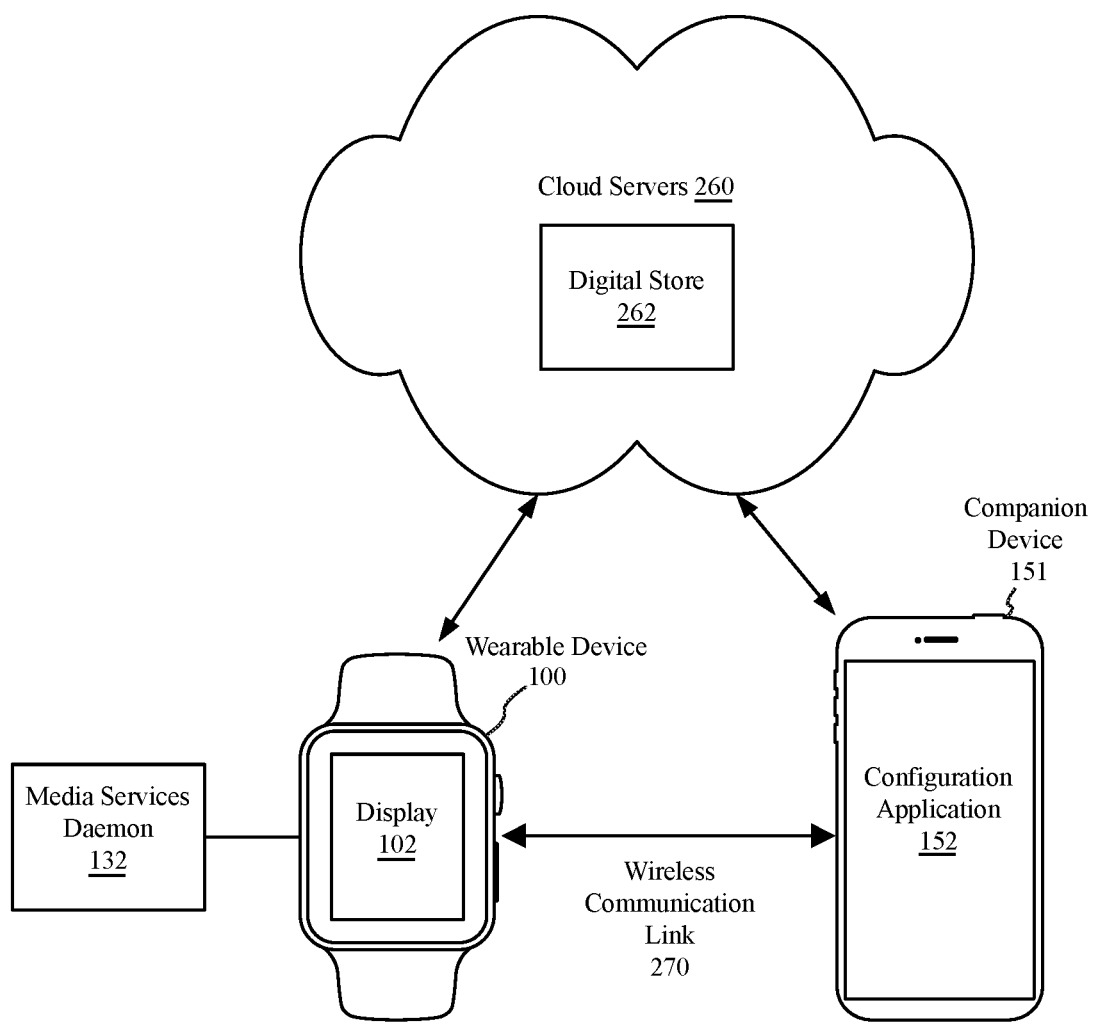
FIG. 2C illustrates elements of an environment to implement a security model and interface for wearable device digital purchases, according to embodiments described herein.

FIG. 2C illustrates elements of an environment 250 to implement a security model and interface for wearable device digital purchases, according to embodiments described herein. Referring to FIG. 2C, in some examples environment 250 may comprise a wearable device 100, a companion device 151, and one or more cloud servers 260 including a cloud-based digital store 262. Wearable device 100 and companion device 151 can be implemented substantially as described above with reference to FIG. 1A and FIG. 1B. Wearable device 100 may be communicatively coupled to companion device 151 by a wireless communication link 270, such as but not limited to a Bluetooth link, an infrared (IR) link, or a Wi-Fi link. Where the wearable device is communicatively coupled to companion device 151 by a Wi-Fi link, the Wi-Fi link can be an infrastructure-based link or a peer-to-peer link. In one embodiment, companion device 151 can be similar to mobile electronic device 130 in FIG. 1B, although other types of devices may be used.

In configurations of the wearable device 100 that are limited to accessing the digital store 262 via the companion device 151, a digital store interface on the companion device 151 is used to download applications and media to the companion device 151. A user may use the digital store on the companion device 151 to download media (e.g., music, television, movies, books, etc.) and to download and install applications. Applications with wearable device versions may be transmitted after download from the companion device 151 to the wearable device 100 over the wireless communication link 270.

Embodiments described herein provide an application and associated user interface to the digital store 262 that is operable on the wearable device 100 without reliance upon the companion device 151. The application and user interface to the digital store 262 enables users of the wearable device 100 to browse and acquire media and applications on directly on the wearable device 100. In many instances, purchases of items on the digital store 262 can be performed on the wearable device 100 without requiring the user to provide input on the companion device 151, although security policies may be configured to enable or require confirmation of purchases via the companion device 151. Additionally, a user having a wearable device 100 that is configured as a standalone device that is not paired with a companion device 151 can access the digital store 262 without requiring the user to have a companion device 151. Access to the digital store 262 is also enabled for users of a wearable device 100 that is paired with a smartphone that does not have access to the digital store 262, such as, for example, a smartphone of a differing vendor or manufacturer as the wearable device 100.

In one embodiment, when an application is downloaded via the interface to the digital store 262 that is presented on the wearable device 100, the application is downloaded directly to the wearable device 100 from the digital store 262, without being downloaded to a companion device 151 and relayed via the wireless communication link. If the wearable device 100 is paired with a companion device 151 and a companion version of the application is available for the companion device, the wearable device 100 can send metadata to the companion device 151 that enables the companion device 151 to download the companion application from the digital store 262. If an application is downloaded via an interface to the digital store on the companion device 151, instead of sending an installation package of the wearable device version of the application the wearable device 100 over the wireless communication link 270, metadata is transmitted over the wireless communication link 270 that enables the companion device to download the application from the digital store 262.

Enabling direct downloads to the wearable device 100 enables the companion device 151 to recover space that would previously be used to store application packages for wearable device versions of applications. Download and install speed for applications on the companion device 151 are increased, as the applications downloaded from the digital store 262 are no longer required to also include versions for the wearable device 100.

Additionally, many instances and version of the wearable device 100 may exist, each with differing capabilities. For example, an initial version of the wearable device 100 may have a 32-bit processor, while an updated version of the wearable device 100 may have a 64-bit processor. The updated version of the wearable device 100 may have sensors that are not present on the initial version of the wearable device 100. Additionally one instance of the updated version of the wearable device 100 may have a different sensor package than another instance and thus may not support some applications. To compensate for this issue, application packages may have been required to include multiple application instances, each configured for execution on the different instances of the wearable device 100. In embodiments provided herein, in response to an application install on the companion device 151, the companion device 151 can transfer metadata to the wearable device 100 over the wireless communication link 270 to identify the installed application. Based on the metadata provided from the companion device 151, the wearable device 100 can make a determination whether to directly download and install the specific version for the hardware and capabilities of the wearable device 100 from the digital store 262 or a digital store repository hosted on the cloud servers 260.

In one embodiment, applications may be compiled to include separate application portions that are specifically configured for operation on one or more versions of the wearable device 100 and/or the companion device 151. The separate portions of the application may be uploaded to the digital store 262 as a single package. The single package may then be thinned (e.g., separated) into the distinct portions. The digital store 262 can provide the portions of the application separately to different devices depending on the device that is performing the download, rather than requiring the companion device 151 to download the superset of the portions and determine which of the portions is to be provided to the wearable device 100.

In one embodiment, the companion device application and the wearable device application may be standalone applications. The application on the wearable device 100 may not require the presence of a companion application that executes on the companion device 151. Installing an application on the wearable device 100 may not automatically trigger a download of a companion version of the application for execution on the companion device 151. Likewise, downloads to the wearable device 100 in response to a download on the companion device 151 may not be automatic. The wearable device 100 can include logic to determine whether or not to download a wearable device version of an application that has been downloaded and installed on the companion device. In one embodiment, determinations on whether to download applications on either the companion device 151 or the wearable device 100 in response to the download and install of an application on the other device may be determined by on-device logic on each device. The on device logic can consider properties set by the application that indicate that whether, for example, a version of the application for the wearable device 100 would benefit from or be interoperable with a version of the application that also executes on the companion device 151. In one embodiment, such determinations can also be overridden based on user-configured settings.

In one embodiment, applications that are capable of standalone operation on the wearable device 100 may be universal applications that can execute on either the wearable device 100 or the companion device 151 in standalone mode. A single application binary may be downloaded to either the wearable device 100 or the companion device 151. The application may configure interface and operational parameters at runtime using runtime platform detection capabilities. The application may also detect the presence of other versions of the application that are executing on nearby devices. For example, a standalone application version on the wearable device 100 may detect the presence of a standalone application version on the companion device 151. The standalone applications may then make a determination as to whether to interact over the wireless communication link 270 or via a connection established via the cloud servers 260.

In one embodiment, the digital store 262 can include logic to determine an optimal delivery mechanism for applications requested for download by a wearable device 100 or a companion device 151. For example, older versions of the wearable device 100 may lack the capability to execute standalone applications and/or may lack the ability to directly access and/or download applications from the digital store 262. In such scenario, the digital store 262 can provide the portion of the application that is executable on the companion device 151 and also provide the portion of the application that can execute on the wearable device 100. In scenarios where the wearable device 100 has the ability to directly download an application from the digital store 262, depending on device context such as battery level, network connection quality, and the availability of a companion device, the wearable device may request that the download be performed by the companion device 151 on behalf of the wearable device. Similarly, based on a measured connection quality between the wearable device 100 and the digital store 262 in comparison to a measured network quality between the digital store and an available companion device 151, the logic on the digital store 262 may determine to relay the download to the wearable device 100 via the companion device 151. A relay through the companion device may also be performed, for example, if the companion device 151 is attached an external power source and/or the wearable device 100 has a low battery level.

In one embodiment, where the wearable device 100 is configured as a standalone device, the digital store 262 may delay provision of a requested application until the wearable device is attached to a charging device, particularly in the instance of large downloads that may be power intensive. This scenario may be of particular relevance or the download is to occur over a cellular connection of the wireless device 100, rather than via a local network (e.g., Wi-Fi connection). A method to determine a download path for applications or media items requested for download by a wearable device 100 is shown in FIG. 2D.

Figure 2D:
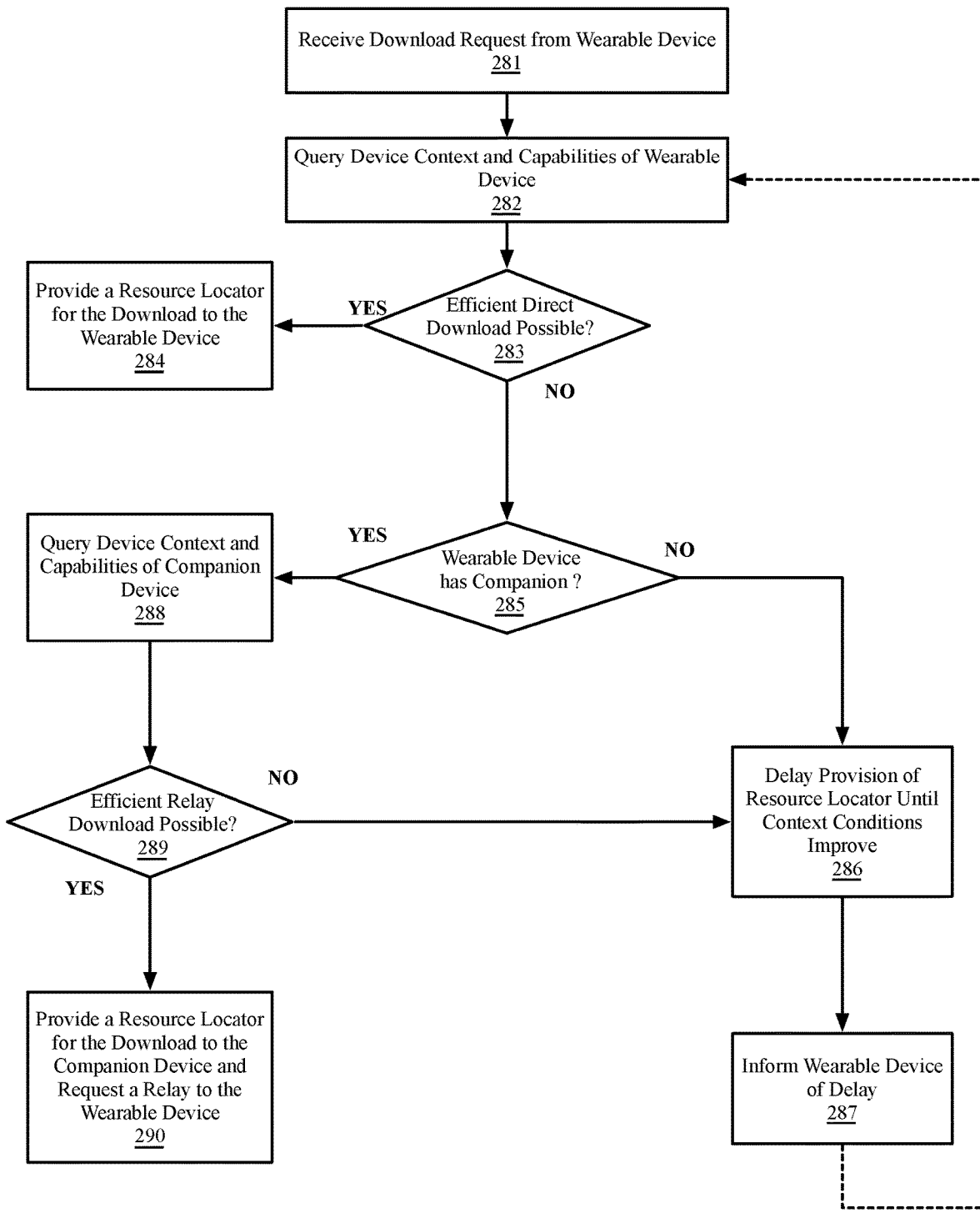
FIG. 2D illustrates a method to enable the context-aware provisioning of downloads for a wearable device, according to an embodiment.

FIG. 2D illustrates a method 280 to enable the context-aware provisioning of downloads for a wearable device, according to an embodiment. Method 280 can be performed on a cloud server 260 that hosts a digital store 262 or download provisioning logic associated with the digital store 262. At operation 281, download provisioning logic can receive a download request from a wearable device. At operation 282 a query of device context and capabilities of the wearable device can be performed. At operation 283 it is determined, based on the context received from the wearable device (e.g., network connection quality, network connection type, type of wearable device, wearable device capability, etc.), whether an efficient direct download to the wearable device is possible. If at operation 283 it is determined that an efficient direct download is possible, control passes to operation 284 to provide a resource locator for the download to the wearable device. If at operation 283 it is determined that an efficient direct download is not possible, control passes to operation 285, where a determination can be made as to whether the wearable device is associated with a companion device. If at operation 285 it is determined that the wearable device has a companion device, the download provisioning logic, at operation 288, can query the device context and capabilities of the companion device to determine if, at operation 289, an efficient relay download is possible. If an efficient relay download is possible, control can pass to operation 290. At operation 290, the download provisioning logic can provide a resource location for the download to the companion device and request that the companion device relay the downloaded data to the wearable device.

If at operation 289 an efficient relay download is determined to not be possible, or at operation 285 the wearable device is a standalone device without a paired companion device, control can pass to operation 286. At operation 286, the provision of the resource download to the wearable device can be delayed until context conditions improve (e.g., network connection quality improves, the wearable connects to a LAN, the wearable is connected to a charger, etc.). The download provisioning logic can mark the download as delayed and periodically check the status of the download. The download may be maintained in a delayed state until a timeout condition occurs. Control can then pass to operation 287, where the download provisioning logic informs the wearable device of the delay. The wearable device can be informed of the reason for the delay and the can present a notice to the user. For example, the notice can inform the user that the download will begin when the user connects to a Wi-Fi network or when the wearable device is placed on a charger. Once the context conditions improve, the wearable device can re-send a request and/or updated context information to the provisioning logic and control can return to operation 282.

Wearable Device Configuration

Companion device 151 can include a configuration application 152 to enable the wearable device 100 to be configured 100 and provisioned. Wearable device 100 can include a media services daemon 132 that facilitates purchases via the digital store 262. The wearable device 100 may be adapted to implement one or more graphic user interfaces (GUIs) to enable users to browse, search, and present media items for purchase and/or download on the digital store 262 via the media services daemon 132. One example of a digital store 262 is described in commonly assigned U.S. Pat. No. 7,774,708, to Bell, et al., entitled GRAPHICAL USER INTERFACE WITH IMPROVED MEDIA PRESENTATION. Another example of a digital store 262 is described in commonly assigned U.S. Pat. No. 8,161,411 to Robbin, et al., entitled GRAPHIC USER INTERFACE FOR BROWSING, SEARCHING, AND PRESENTING MEDIA ITEMS. The contents of these applications are incorporated herein by reference in their entirety.

Digital store 262 may execute one or more processes to authenticate users and/or devices in the environment 250. In some examples digital store 262 executes an authentication process to authenticate a password equivalent token (PET) associated with wearable device 100. In some examples digital store 262 also executes an identification authentication process to authenticate an identification token associated with the wearable electronic device 100. These features are described in greater detail below.

Figure 3A:
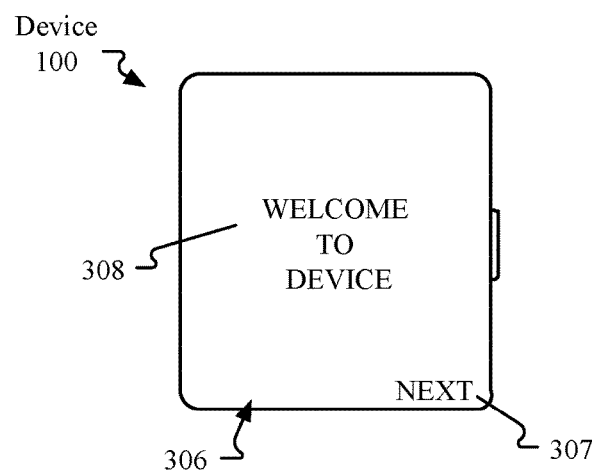
FIG. 3A-3C illustrate exemplary welcome and instruction screens for a wearable device.

FIG. 3A shows an exemplary welcome screen 306 that a device 100 can display on its display. Device 100 may transition from displaying a boot-up screen to displaying welcome screen 306 after at least a portion of the boot-up process has completed. Welcome screen 306 may include a welcome message 308 containing any desired text, image, icon, animation, video, or the like. Welcome screen 306 may also include an affordance 307 showing the text "NEXT". As used herein, the term "affordance" refers to a user-interactive graphical user interface object that may be displayed on the display screen of device 100. For example, an image (e.g., icon), a button, and text (e.g., hyperlink) may each constitute an affordance. In some embodiments, a user may select an affordance via a mouse gesture (e.g., hover, click, double-click, drag). In some embodiments, a user may select an affordance via a touch-based gesture (e.g., tap, swipe, flick, long touch).

A user may select the displayed affordance 307 to instruct device 100 to continue to the next step or screen in the initialization process. For example, in response to a tap gesture on affordance 307, electronic device 100 may continue the initialization process. Alternatively, a user may cause the electronic device 100 to transition to the next screen or continue the initialization process by a swipe gesture from right to left on the touch-sensitive display or using the rotatable input mechanism 301.

In one embodiment, electronic device 100 continues the initialization process by transitioning the display to an optional personalized message screen. A personalized message screen may include a personalized message containing any desired text, image, icon, animation, video, or the like.

Figure 3B:
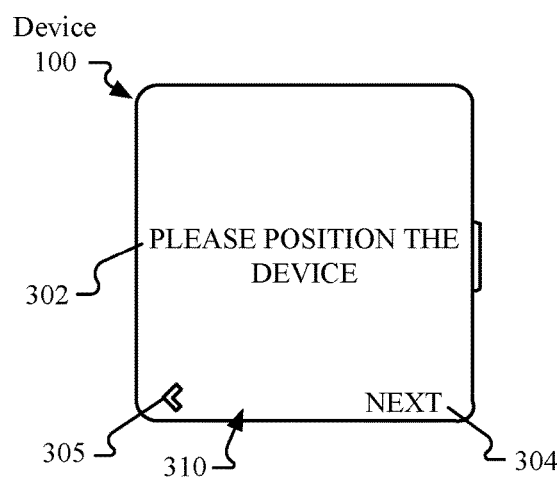

FIG. 3B shows an exemplary instruction screen 310 that device 100 can display on its display is described. The instruction screen 310 may include an image, icon, animation, video, text, or the like that prompts the user to take an action. For example, instruction screen 310 includes text 302 instructing the user to position the device. In one embodiment, a user may be instructed to attach the electronic device 100 to a body part such as one of the user's wrist.

Instruction screen 310 also includes affordances 304 and 305. Affordance 304 has an icon including the text "NEXT". Selecting affordance 304 may instruct device 100 to continue to the next step or screen. That is, in response to a tap gesture on affordance 304, electronic device 100 continues the setup process. A user may select affordance 304 to indicate that the user has complied or intends to comply with the instruction text 302. In an alternate embodiment, the device detects, using one or more biometric sensors, that the user has positioned the device and advances to screen 320 without the need for user contacting affordance 304. Affordance 305 includes an icon of an arrow head pointing to the left. A user may select affordance 305 to cause device 100 to display the previous screen. That is, in response to a tap gesture on affordance 305, electronic device 100 returns to a previous step or displays a screen displayed prior to screen 310.

Figure 3C:
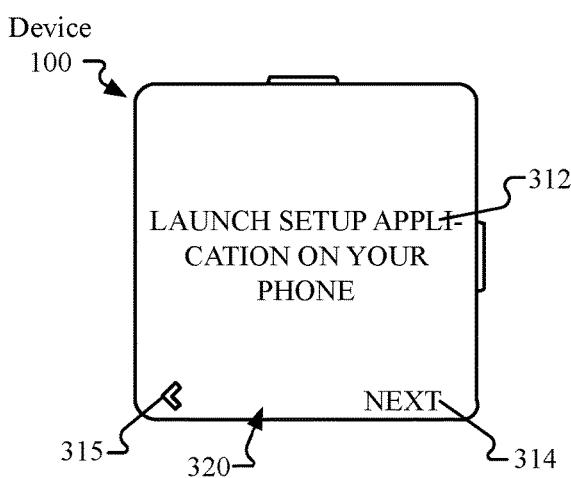

FIG. 3C shows another exemplary instruction screen 320 that device 100 can display on its display. Instruction screen 320 may be displayed to prompt a user to take an action that will initiate pairing of the electronic device 100 with an external electronic device, such as the mobile electronic device 130 of FIG. 1B.

The external device may operate in a pairing mode that allows it to pair with another device, such as device 100. As used herein, pairing mode refers to an operating mode in which two devices attempt to register one another for future wireless communications. For example, the process of initially connecting two Bluetooth-enabled devices involves entering into pairing mode on the devices.

In some embodiments, wireless communication, for purposes of pairing, occurs over a peer-to-peer wireless communication protocol such as Bluetooth and/or Bluetooth Low Energy (BTLE). In some embodiments, wireless communication for purposes of pairing functionality utilizes more than one wireless communication protocol. For example, Wi-Fi may be used in addition to BTLE. In these embodiments, an initial communication between two devices may occur over a lower powered protocol, such as BTLE, even if the protocol yields a slower data transfer speed. Subsequent communications may occur over a secondary network that is relatively faster, such as Wi-Fi.

The pairing mode of the external device may be invoked by running a software program. The software program may be part of an operating system or an application program. In one embodiment, the external device displays an affordance (e.g., a selectable icon) representing an application for pairing the external device with another device (e.g., device 100). Selecting the application affordance may launch the application and invoke the pairing mode.

In some embodiments, the application affordance is displayed on the external device only when device 100 is within communication range of the external device. For example, device 100 may wirelessly transmit data that represents a request to pair or that indicates it is capable of pairing with another device. If the external device is not within communication range, the affordance is not displayed. However, if the external device receives the data, and therefore is within communication range of device 100, then the application affordance is displayed.

In another embodiment, when the external device is not within range, the application affordance is displayed but in a manner that indicates that the application cannot be launched. For example, the application affordance may appear greyed-out or semi-transparent to indicate that the application cannot be launched. When the external device comes within communication range of device 100, the visual appearance of the application affordance may be changed to indicate that the application can be invoked.

Instruction screen 320 includes text 312 instructing the user to launch an application on the user's phone to pair the device 100. In one embodiment, the application is launched by executing a tap gesture on an affordance associated with the application displayed on the user's phone. The application may invoke a wireless communications pairing mode for pairing the device 100 with the user's phone.

Instruction screen 320 also includes affordances 314 and 315. Affordance 314 has an icon including the text "NEXT". Selecting affordance 314 may instruct device 100 to continue to the next step or screen. That is, in response to a tap gesture on affordance 314, electronic device 100 continues the setup process. Accordingly, a user may select affordance 314 to indicate that the user has complied or intends to comply with the instruction text 312. That is, selecting affordance 314 may indicate that the user has or intends to launch an application program for pairing the phone with the electronic device. Affordance 315 includes an icon of an arrow head pointing to the left. A user may select affordance 315 to cause device 100 to display the previous screen. That is, in response to a tap gesture on affordance 315, electronic device 100 returns to a previous step or displays a screen displayed prior to screen 320.

FIG. 4A shows an additional instruction screen 400 that device 100 can display on its display. Instruction screen 400 may be displayed after screen 320 of FIG. 3C to facilitate setup of the device 100 via an external device 450. Instruction screen 400 includes text 402 instructing the user to take a picture of instruction screen 400 with a camera on the external device 450 or to otherwise position device 100 such that device 100 is visible to the camera of the external device 450.

Instruction screen 400 also includes an image containing a pattern 404. The displayed image may include wavelengths that are visible to the human eye. The image may also include wavelengths that are invisible to the human eye but can be produced by the display on device 100 and detected by the camera of external device 450. In one embodiment, the instruction screen 400 may display an invisible image containing the pattern 404 along with a visible image. The visible image may be aesthetically appealing to the user, while the invisible image may contain information that can be and/or is easier to recognize and/or process by a processor facilitating the pairing.

The pattern 404 may be used to identify or authenticate the device 100. In one embodiment, the pattern comprises identifying information of the device 100. Identifying information may include any design, symbol, pattern, sequence, indication, or the like that identifies the device 100, such as a quick response code or a bar code. The identifying information may be unique to device 100 or may generally indicate the type of device.

FIG. 4B shows an external device 450 that may be paired or associated with device 100. Device 100 can be paired with the external device 450 or can be configured for a user other than the user of the external device 450. When device 100 is configured for another user, device 100 can be configured as a satellite device that is not directly paired with but may be at least partially managed by the external device 450. For example, device 100 can be configured as a device to be worn by a child or other minor-aged relative of the user associated with the external device 450.

In one embodiment, external device 450 is a phone with a camera that may be used to take a picture of device 100 while instruction screen 400 is displayed. Using the camera of external device 450, a user may obtain an image containing a visual representation of the device 100 including the pattern 404 displayed on the screen of electronic device 100. External device 450 displaying an example of an obtained image 452 of electronic device 100. Image 452 shows electronic device 100 displaying instruction screen 400 with the pattern 404.

External device 450 may process the obtained image 452 to extract the identifying information contained in the pattern 404. External device 450 may then use the extracted identifying information to authenticate the device 100 for pairing. In one embodiment, the electronic device 100 transmits data via wireless communication. The data may include information identifying the electronic device 100. The data may also include information representative of the pattern displayed on screen 400. Electronic device 100 may send the data in response to an indication that the user has launched or intends to launch an application program for pairing the user's phone with device 100 (e.g., selecting affordance 314 on screen 310 as described above).

The external device 450 may receive the data transmitted by electronic device 100 and determine whether the identifying information in the received data corresponds with the identifying information in the image of the pattern obtained by the camera. If the external device 450 determines that the received data corresponds with the identifying information in pattern 404, then the external device 450 may register device 100 as an associated device. Alternatively, if the external device 450 determines that the received data does not correspond with the identifying information in pattern 404, then the external device 450 may not register device 100 as a paired or associated device.

FIG. 4C shows an exemplary instruction screen 460 that device 100 can display on its display. Instruction screen 460 includes text 462 instructing the user to tap the user's phone with the device 100 to initiate setup of the device. In one embodiment, external device 450 and device 100 can be brought into close contact (e.g., via a tap) to enable an exchange of data via an NFC connection. The data exchanged can include identifying information of device 100 and keys or passcodes that can be used to establish a secure wireless connection via, for example, Bluetooth or Wi-Fi. In response to receiving the data transmitted by the device 100 and the external device 450 may register device 100 as a paired device or set up device 100 as a standalone or satellite device. The data exchange facilitated via NFC can be done in addition to as an alternative to the image-based data exchange shown in FIG. 4A-4B.

Once the device 100 has connected with the external device 450, the device 100 and/or the external device 450 may provide an indication that the devices have paired. The indication may include an aural indication, such as a chime, ping, beep, tune, or the like. The indication may also, or alternatively, include a haptic indication, such as tactile feedback in the form of buzzing, vibrating, or pulsing. In one embodiment, each device provides an indication simultaneously with the other. In another embodiment, the devices provide indications one after the other in a back-and-forth manner which indicates that the two devices are in sync.

Security Model for Digital Purchases on a Wearable Device

Figure 5:
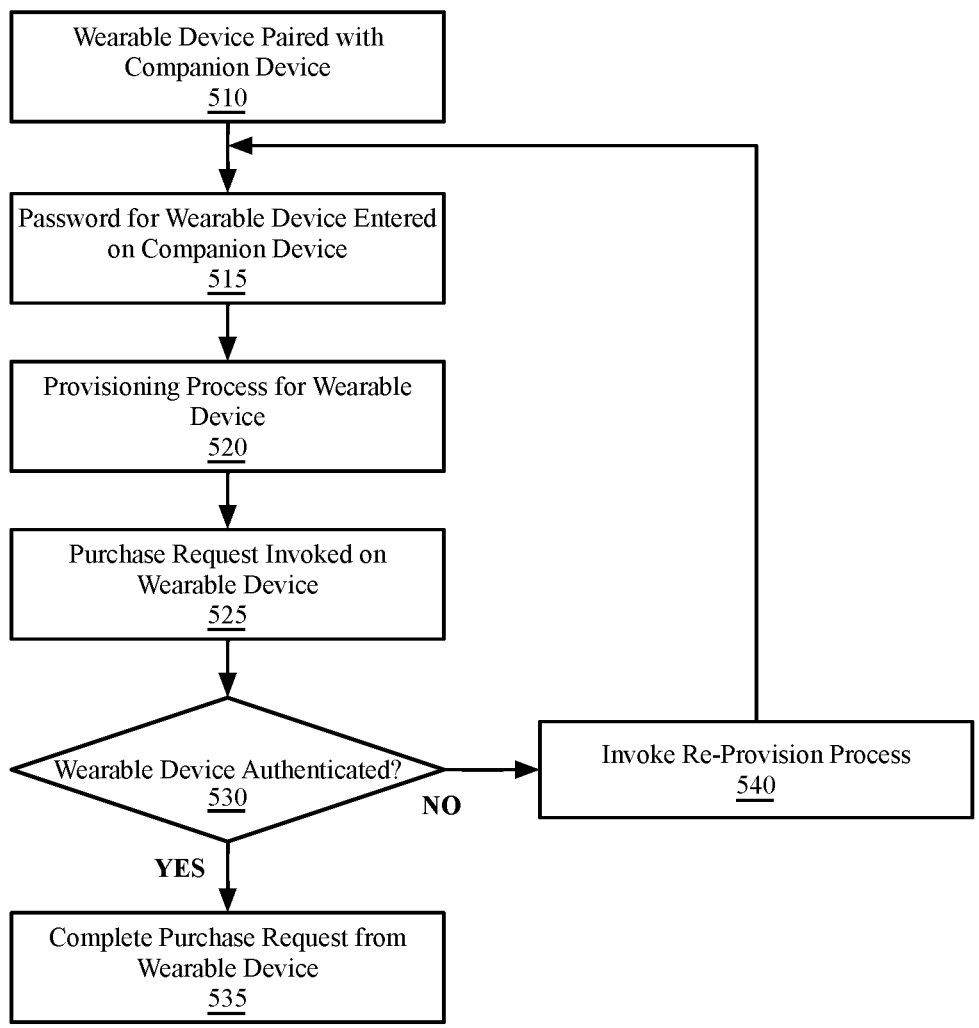
FIG. 5 illustrates operations implemented in a method to implement a security model and interface for wearable device digital purchases, according an embodiment.

FIG. 5 illustrates high-level operations implemented in a method 500 to implement a security model and interface for wearable device digital purchases, according to embodiments described herein. Referring to FIG. 5, in some examples a wearable device such as wearable device 100 may be paired with a companion device such as companion device 510 using techniques as described above with reference to FIGS. 4A, 4B, and 4C. At operation 515 a password for the wearable device 100 is entered on the companion device, and at operation 520 a provisioning process is implemented to provision the wearable device 100 to make purchases from a digital shopping store is implemented.

At operation 525 a purchase request is invoked on the wearable device. In response to the purchase request, at operation 530, it is determined whether the wearable device 100 is authenticated to make a purchase transaction. If, at operation 530, the wearable device 100 is authenticated then the method advances to operation 535 and the purchase request is completed from the wearable device 100. By contrast, if at operation 530 the wearable device 100 is not authenticated then the method can invoke the re-provision process 540 and return to operation 515 to allow a user to repeat the password entry and provisioning processes for the wearable device 100. The various operations depicted in FIG. 5 are described in greater detail in FIGS. 6-8.

Figure 6:
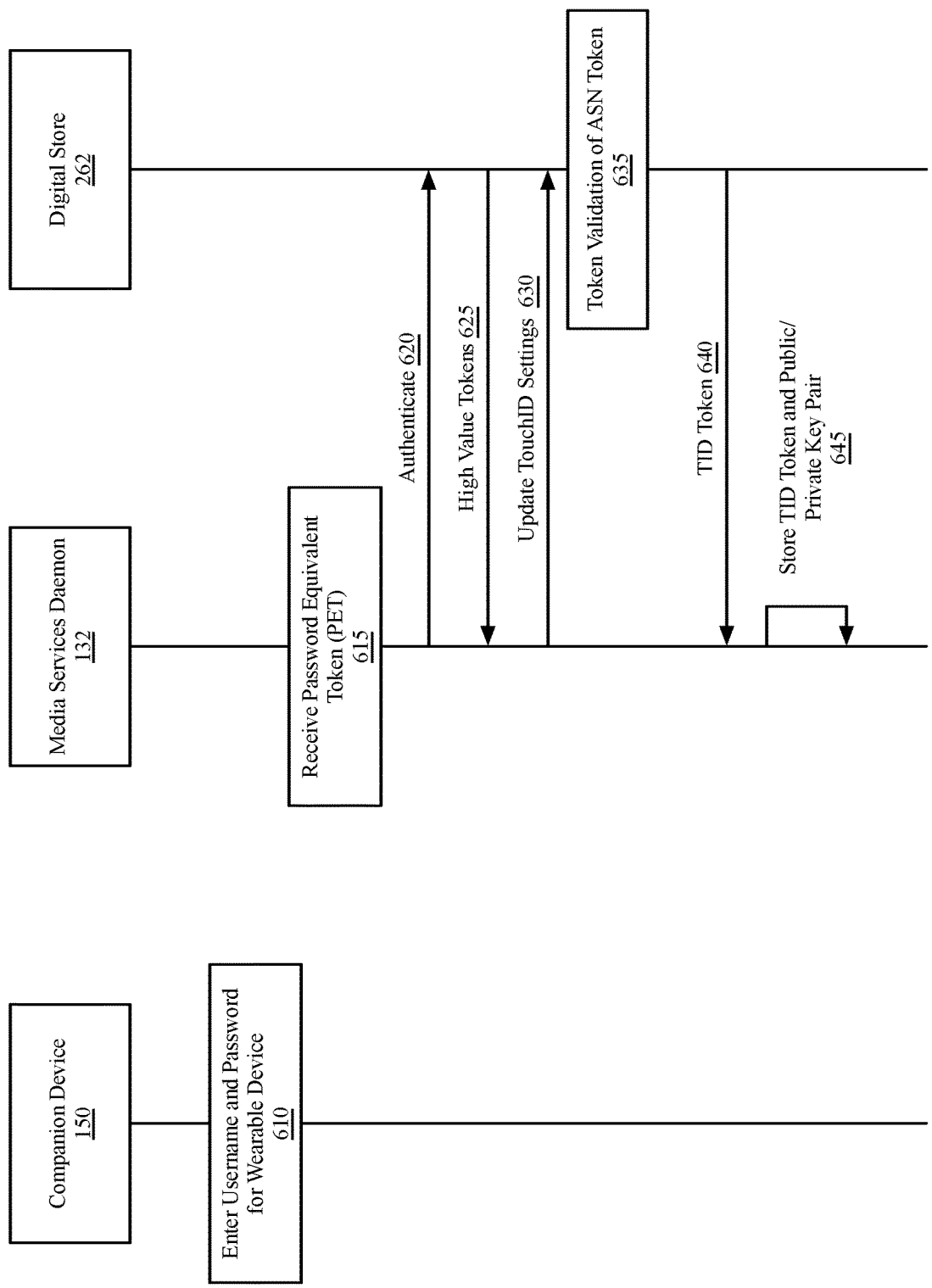
FIG. 6-8 illustrate methods to implement a security model and interface for wearable device digital purchases, according to embodiments described herein.

FIG. 6 illustrates a method 600 for provisioning a wearable device such as wearable device 100 to make purchases. Referring to FIG. 6, in some examples a provisioning process involves a companion device such as companion device 150, a media services daemon 132, and a digital store 262. At operation 610 a user enters the username and password for the wearable device 100 into the companion device 150. The username and password may be transmitted from the companion device 150 to the wearable device 100 via the wireless communication link 270 depicted in FIG. 2C. In some examples operation 610 may have been performed previously during a setup and/or configuration process, in which case operation 610 need not be implemented separately during the provisioning process. In other examples the provisioning process depicted in FIG. 6 may be implemented as part of a setup/configuration process when a wearable device 100 is first paired with a companion device 150.

In some examples a token referred to as a password equivalent token (PET) may be generated from the username and/or password, e.g., by applying one or more hash functions to the username and/or password. At operation 615 the PET is provided to a media services daemon 132. At operation 620 the media services daemon 132 initiates a password authentication request with a password authentication process that executes on digital store 262. The username and/or PET may be forwarded to the password identification authentication process with the authentication request 620.

In the event that the password authentication request 620 is successful, the password authentication process returns one or more high value tokens 625 in response to the authentication request 620. In some examples at least one of the tokens comprises an ASN (always, sometimes, never) token which enables a configurable password request routine for a user. The ASN token may be configured to always ask for a user password (e.g., with every purchase transaction initiated by a user), to sometimes ask for a user password (e.g., on a defined, periodic basis), or to never ask for a user password.

At operation 630 the media services daemon 132 initiates a call to a process to update the TouchID settings for the wearable device 100 with the ASN token. In some examples the media services daemon 132 may generate a public/private key pair and the public key is transmitted with the request.

At operation 635 the ASN token is validated by the digital store 262. In some examples the digital store 262 validates the ASN token and confirms that the public key was generated on a device that is whitelisted (i.e., a valid and approved device). If the validation is successful, then at operation 640 the digital store 262 returns a TouchID (TID) token.

At operation 645 the TID token is stored in a computer-readable memory in association with account authentication tokens for the account on the wearable device. The public/private key pair can be stored in a secure processor, such as a secure enclave processor (SEP), on the wearable device 100. Other types of secure processors may also be used.

Figure 7:
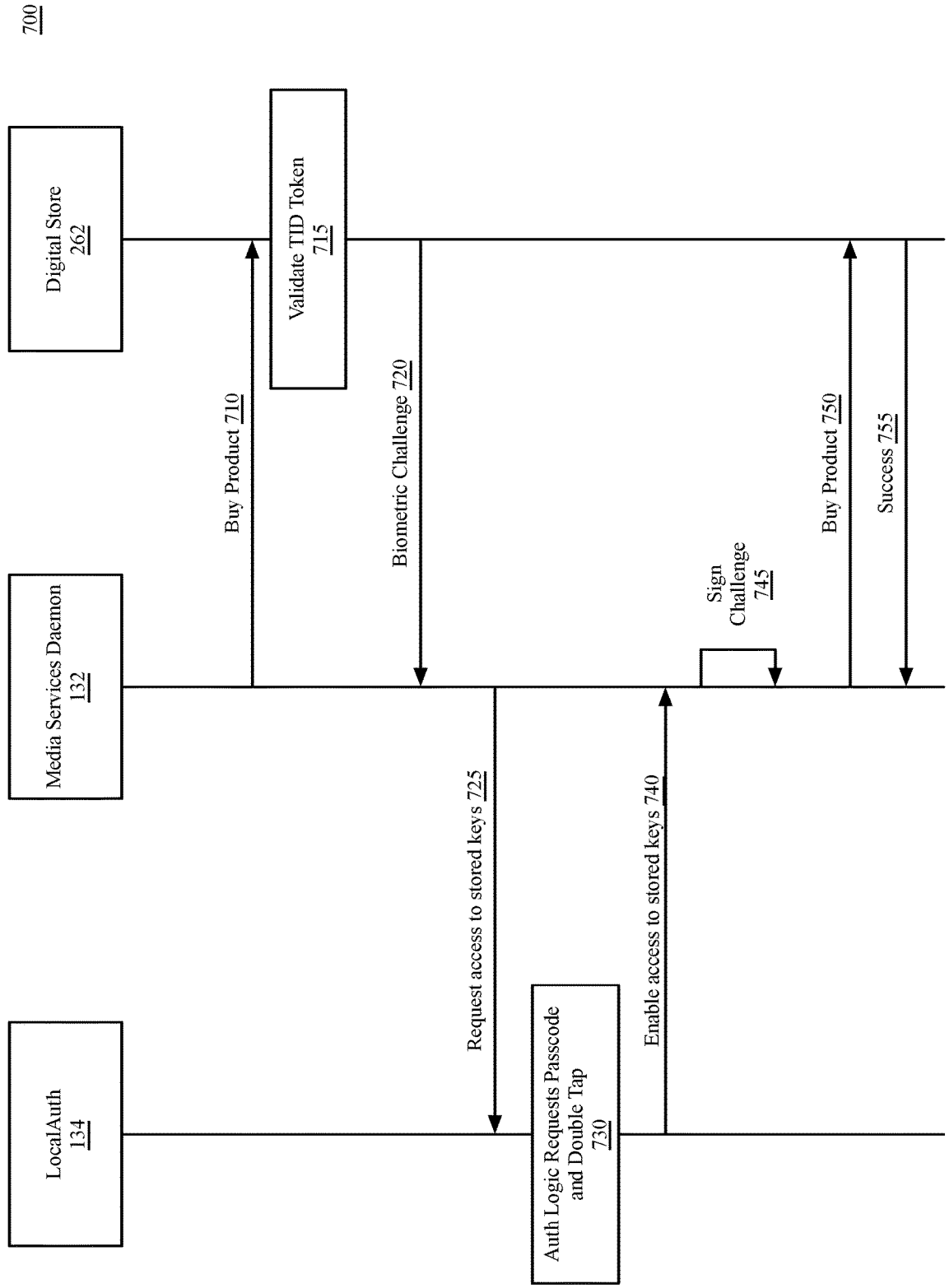

FIG. 7 illustrates a method 700 to use a wearable device to effect secure purchases from a digital store 262 without support from an associated companion electronic device 150. Referring to FIG. 7, the process begins when a user of wearable device 100 initiates a purchase transaction request at a digital shopping store using an interface on the wearable device 100. The media services daemon 132 receives the request from the interface on the wearable device 100 and in response, at operation 710, sends a corresponding purchase request including the TID token and may include one or more of the account tokens to an identification authentication process that executes on the digital store 262.

At operation 715 the identification authentication process on the digital store 262 validates the TID token and any other tokens included with the request. At operation 720 the digital store 262 responds with a biometric challenge. The biometric challenge can include a data blob that is to be signed using keys of the wearable device to determine the authenticity of the purchase request.

In response to the biometric challenge, at operation 725, the media services daemon 132 launches a request to the local authentication interface 134 of the wearable device 100 to enable access to the public/private keys stored in the secure processor of the wearable device 100. In response to the request, authentication logic requests a user to enter their passcode and to apply a double tap on the wearable device (operation 730). The double tap can instead be any physical input that validates an intent of the user to purchase a product via the digital store 262. If the wearable device 100 has a companion device, additional biometrics may be requested at the companion device, such as biometrics based on facial recognition or fingerprint recognition. In response, at operation 740, the local authentication interface 134 enables the public/private keys stored in the secure processor to be unlocked for use by the media services daemon 132.

At operation 745 the media services daemon 132 uses one or more of the public/private keys to sign the biometric challenge, which is returned to the identification authentication process on the digital store 262 with a replay of the buy product request 750. The digital store 262 can, for example, use the public key of the wearable device to authenticate the signature, which was generated using the wearable device using a private key. At operation 755 the digital store 262 response with a success indicator if the signature on the challenge is valid.

Figure 8:
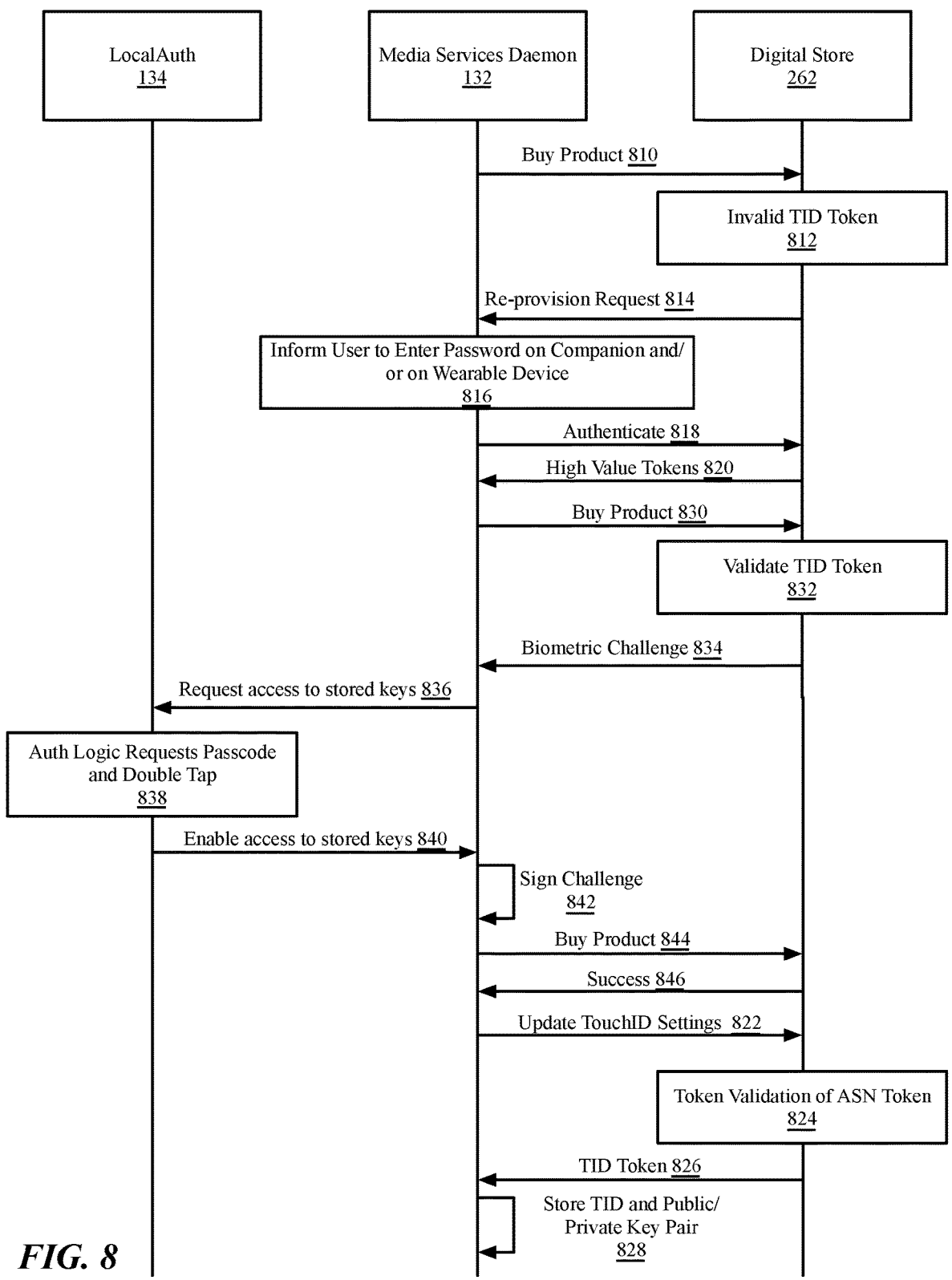

FIG. 8 illustrates a method 800 to use a wearable device 100 to effect secure purchases from a digital shopping store 262 without support from an associated companion device 150. Referring to FIG. 8, the process begins when a user of wearable device 100 initiates a purchase transaction request at a digital store 262 using the wearable device 100. The media services daemon 132 receives the request from an interface on the wearable device 100 and in response, at operation 810, sends a corresponding purchase request including the TID token and may include one or more of the account tokens to an identification authentication process that executes on the digital store 262.

At operation 812 the identification authentication process on the digital store 262 concludes that the TID token is invalid, and in response at operation 814 the identification authentication process on the digital store 262 responds with a request to re-provision the wearable device 100 for purchases. At operation 816 the media services daemon 132 informs the user of the wearable device 100 to enter the password on the companion device 150. Alternatively, or in addition, the user of the wearable device 100 may be offered the opportunity to enter the password directly on the wearable device. If a non-companion device is nearby that can be used remote interface device, the keyboard of the non-companion device can be used for credential entry. Additionally, dictation may be used for credential entry.

As described above with reference to the provisioning process of FIG. 6, a user enters the username and password for the wearable device 100 into the companion device 150 (or alternatively into the wearable device 100). At operation 818 the media services daemon 132 initiates an authentication request with an authentication process that executes on digital store 262. The username and/or PET may be forwarded to the password authentication process with the authentication request 818.

In the event that the password authentication request 818 is successful, the authentication process returns one or more high value tokens 820 in response to the authentication request 818. In some examples at least one of the tokens comprises an ASN (always, sometimes, never) token which enables a configurable password request routine for a user. The ASN token may configure the authentication process always asks for a user password (e.g., with every purchase transaction initiated by a user), to sometimes ask for a user password (e.g., on a defined, periodic basis), or to never ask for a user password.

At operation 830 the media services daemon 132 sends a purchase request including the updated TID token and one or more of the account tokens to the identification authentication process that executes on the digital store 262.

At operation 832 the identification authentication process on the digital store 262 validates the TID token and any other tokens included with the request 830. At operation 834 the digital store 262 responds with a biometric challenge.

In response to the biometric challenge, at operation 836, the media services daemon 132 launches a request to the local authentication interface 134 of the wearable device 100 to enable access the public/private keys stored in the secure processor on the wearable device 100. In response to the request, the authentication logic requests the user to enter their passcode and to apply a double tap or another physical input on the wearable device (operation 838). In response, at operation 840, the local authentication interface enables access to the public/private keys for the wearable device 100 to the media services daemon 132.

At operation 842 the media services daemon 132 uses one or more of the public/private keys to sign the biometric challenge, which is returned to the identification authentication process on the digital store 262 with a replay of the buy product request 844. At operation 846 the digital store 262 can respond with a success indicator if the signature is valid.

Once a purchase is successfully performed, at operation 822 the media services daemon 132 initiates a call to a process to update the TouchID settings for the wearable device 100 with the ASN token. In some examples the media services daemon 132 may generate a public/private key pair and the public key is transmitted with the request.

At operation 824 the ASN token is validated by the digital store 262. In some examples the digital store 262 validates the ASN token and confirms that the public key was generated on a device that is whitelisted (i.e., an approved device). If the validation is successful, then at operation 826 the digital store 262 returns a TouchID (TID) token. The TID token is not limited for scenarios in which touch-based biometrics are used and can generally be used when any form of biometric or action-based authentication is in use.

At operation 828 the TID token is stored in a computer-readable memory in association with authentication tokens for the account on the wearable device. The public/private key pair can be stored to the secure processor of the wearable device 100. Storing TID and public/private key re-enables subsequent purchases using a device passcode, instead of requiring entry of a username/password combination.

Interface for Digital Purchases on a Wearable Device

Figure 9A:
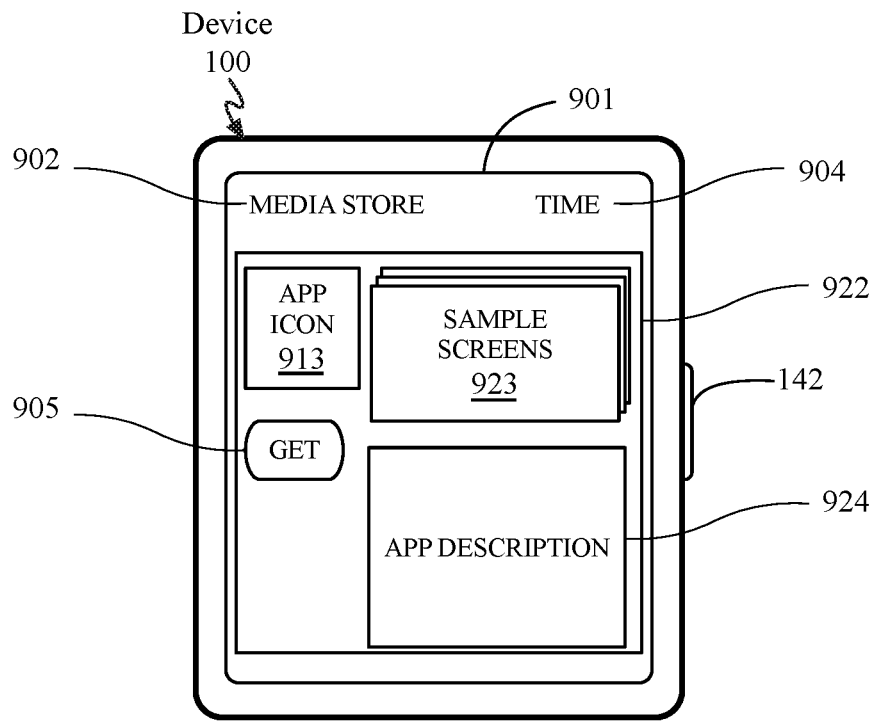
FIG. 9A illustrates user interface details for a media store presented on a wearable device, according to an embodiment.
Figure 9B:
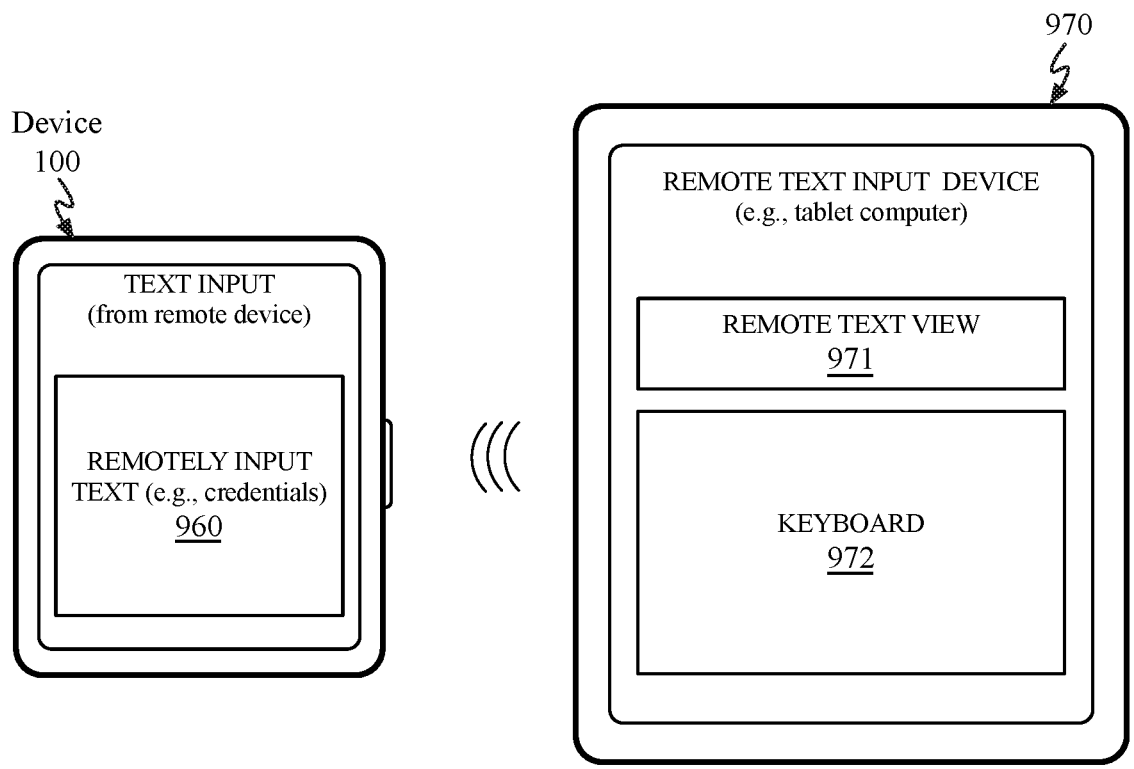
FIG. 9B illustrates remote text entry for a wearable device that may be used to facilitate searches for a media store on the wearable device.

FIG. 9A-9B illustrate user interface details for a media store presented on a wearable device, according to an embodiment. FIG. 9A illustrates an example media store interface that can be presented on a wearable device. FIG. 9B illustrates remote text entry on a wearable device.

As shown in FIG. 9A, device 100 can execute instructions for an application that presents a user interface 901 that enables a user to purchase applications and media items on a wearable device without requiring the use of a companion device. The user interface 901 can provide an interface mechanism for a standalone wearable device media store that can be used when device 100 is a standalone wearable device that is not paired with a companion device. User interface 901 can also be presented in a configuration in which device 100 is paired with an untrusted device, such as a smartphone that is not able to be configured as a trusted device of the digital store 262.

The user interface 901 can present a media store interface that is part of a media purchase system that provides support for the purchase of a large number of media items. The user interface 901 can provide the ability to browse, sort, and search the available media items that are available on the digital store 262. The user interface 901 can present one or more interface windows (e.g., interface window 922) that present content based on information provided by the digital store 262. The user interface 901 can include an interface element 902 that identifies the UI as a media store interface. Where device 100 is an electronic watch device or can otherwise be configured as a timekeeping device, an interface element 904 can be presented to display a current time. Device 100 can also display one or more media store windows, such the exemplary interface window 922 that presents information about and enables the purchase of an application to be downloaded and executed on device 100. User interface 901 can also be configured to enable the purchase of music or the selection and acquisition of other media items (e.g., podcasts, etc.).

Exemplary interface window 922 can include an application icon 913, one or more sample screens 923 that show sample interfaces of an application, and an application description 924. A user interface element 905 can also be presented to enable the acquisition (e.g., purchase) and download of the presented application. Upon acquisition, the selected application or media item can be downloaded to device 100. Interaction with the interface window 922 or other aspects of the interface may also be facilitated via other input mechanisms on the wearable device, such as but not limited to a crown 142.

As shown in FIG. 9B, text input for device 100 can be provided by a remote text input device 970, such as a tablet computer. In one embodiment a laptop or desktop computer can also be used as a remote input device. Remote text input can be enabled, for example, when credentials (e.g., username/password) are to be entered into device 100 and the device is located near an eligible potential remote text input device 970. The remote text input device 970 may also facilitate the interaction with a media store user interface on the wearable device, such as the media store user interface of FIG. 9A.

A remotely input text region 960 of the user interface of device 100 can display text that is received from the remote text input device 970. In one embodiment, in addition to a software-based keyboard 972 that can be displayed on the user interface of the remote text input device 970, the user interface can also display a view 971 of the remote text that has been input by the remote text input device 970, for example if device 100 is a smartwatch or another device that may be difficult to view while in the act of entering remote text.

Additional Exemplary Device Architectures

Embodiments described herein include one or more application programming interfaces (APIs) in an environment in which calling program code interacts with other program code that is called through one or more programming interfaces. Various function calls, messages, or other types of invocations, which further may include various kinds of parameters, can be transferred via the APIs between the calling program and the code being called. In addition, an API may provide the calling program code the ability to use data types or classes defined in the API and implemented in the called program code.

An API allows a developer of an API-calling component (which may be a third-party developer) to leverage specified features provided by an API-implementing component. There may be one API-calling component or there may be more than one such component. An API can be a source code interface that a computer system or program library provides in order to support requests for services from an application. An operating system (OS) can have multiple APIs to allow applications running on the OS to call one or more of those APIs, and a service (such as a program library) can have multiple APIs to allow an application that uses the service to call one or more of those APIs. An API can be specified in terms of a programming language that can be interpreted or compiled when an application is built.

Generally, an API can be used to access a service or data provided by the API-implementing component or to initiate performance of an operation or computation provided by the API-implementing component. By way of example, the API-implementing component and the API-calling component may each be any one of an operating system, a library, a device driver, an API, an application program, or other module (it should be understood that the API-implementing component and the API-calling component may be the same or different type of module from each other). API-implementing components may in some cases be embodied at least in part in firmware, microcode, or other hardware logic. In some embodiments, an API may allow a client program to use the services provided by a Software Development Kit (SDK) library. In other embodiments an application or other client program may use an API provided by an Application Framework. In these embodiments the application or client program may incorporate calls to functions or methods provided by the SDK and provided by the API or use data types or objects defined in the SDK and provided by the API. An Application Framework may in these embodiments provide a main event loop for a program that responds to various events defined by the Framework. The API allows the application to specify the events and the responses to the events using the Application Framework. In some implementations, an API call can report to an application the capabilities or state of a hardware device, including those related to aspects such as input capabilities and state, output capabilities and state, processing capability, power state, storage capacity and state, communications capability, etc., and the API may be implemented in part by firmware, microcode, or other low level logic that executes in part on the hardware component.

Figure 10:
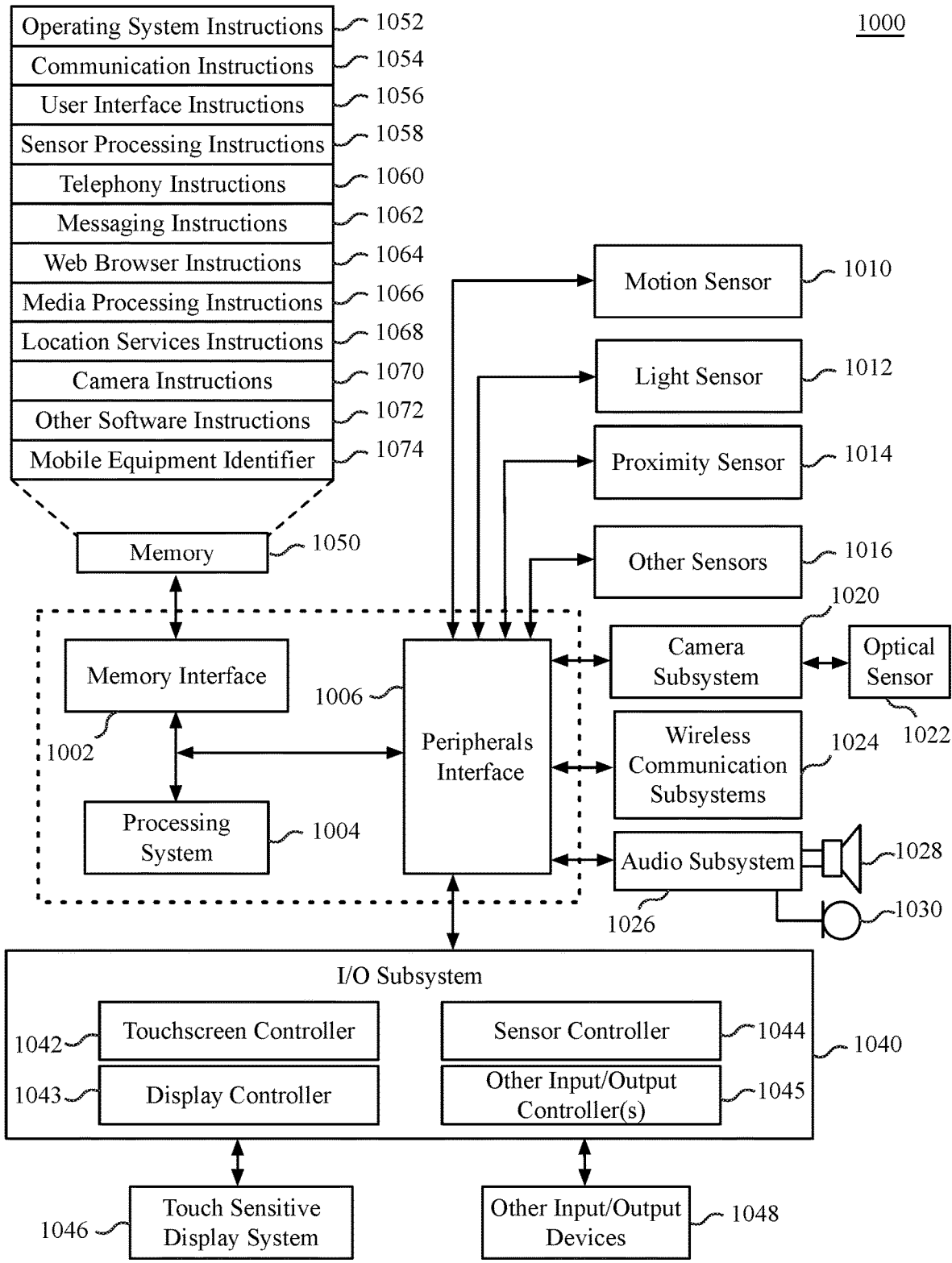
FIG. 10 is a block diagram of mobile device architecture.

FIG. 10 is a block diagram of mobile device architecture 1000, according to an embodiment. The mobile device architecture 1000 includes a memory interface 1002, a processing system 1004 including one or more data processors, image processors and/or graphics processing units, and a peripherals interface 1006. The various components can be coupled by one or more communication buses or signal lines. The various components can be separate logical components or devices or can be integrated in one or more integrated circuits, such as in a system on a chip integrated circuit.

The memory interface 1002 can be coupled to memory 1050, which can include high-speed random-access memory such as static random-access memory (SRAM) or dynamic random-access memory (DRAM) and/or non-volatile memory, such as but not limited to flash memory (e.g., NAND flash, NOR flash, etc.).

Sensors, devices, and subsystems can be coupled to the peripherals interface 1006 to facilitate multiple functionalities. For example, a motion sensor 1010, a light sensor 1012, and a proximity sensor 1014 can be coupled to the peripherals interface 1006 to facilitate the mobile device functionality. Other sensors 1016 can also be connected to the peripherals interface 1006, such as a positioning system (e.g., GPS receiver), a temperature sensor, a biometric sensor, or other sensing device, to facilitate related functionalities. A camera subsystem 1020 and an optical sensor 1022, e.g., a charged coupled device (CCD) or a complementary metal-oxide semiconductor (CMOS) optical sensor, can be utilized to facilitate camera functions, such as recording photographs and video clips.

Communication functions can be facilitated through one or more wireless communication subsystems 1024, which can include radio frequency receivers and transmitters and/or optical (e.g., infrared) receivers and transmitters. The specific design and implementation of the communication subsystems 1024 can depend on the communication network(s) over which a mobile device is intended to operate. For example, a mobile device including the illustrated mobile device architecture 1000 can include wireless communication subsystems 1024 designed to operate over a GSM network, a CDMA network, an LTE network, a Wi-Fi network, a Bluetooth network, or any other wireless network. In particular, the wireless communication subsystems 1024 can provide a communications mechanism over which a client browser application can retrieve resources from a remote web server.

An audio subsystem 1026 can be coupled to a speaker 1028 and a microphone 1030 to facilitate voice-enabled functions, such as voice recognition, voice replication, digital recording, and telephony functions.

The I/O subsystem 1040 can include a touch screen controller 1042 and/or other input controller(s) 1045. The touch screen controller 1042 can be coupled to a touch sensitive display system 1046 (e.g., touch-screen). The touch sensitive display system 1046 and touch screen controller 1042 can, for example, detect contact and movement and/or pressure using any of a plurality of touch and pressure sensing technologies, including but not limited to capacitive, resistive, infrared, and surface acoustic wave technologies, as well as other proximity sensor arrays or other elements for determining one or more points of contact with a touch sensitive display system 1046. Display output for the touch sensitive display system 1046 can be generated by a display controller 1043. In one embodiment the display controller 1043 can provide frame data to the touch sensitive display system 1046 at a variable frame rate.

In one embodiment a sensor controller 1044 is included to monitor, control, and/or processes data received from one or more of the motion sensor 1010, light sensor 1012, proximity sensor 1014, or other sensors 1016. The sensor controller 1044 can include logic to interpret sensor data to determine the occurrence of one of more motion events or activities by analysis of the sensor data from the sensors.

In one embodiment the I/O subsystem 1040 includes other input controller(s) 1045 that can be coupled to other input/control devices 1048, such as one or more buttons, rocker switches, thumb-wheel, infrared port, USB port, and/or a pointer device such as a stylus, or control devices such as an up/down button for volume control of the speaker 1028 and/or the microphone 1030.

In one embodiment, the memory 1050 coupled to the memory interface 1002 can store instructions for an operating system 1052, including portable operating system interface (POSIX) compliant and non-compliant operating system or an embedded operating system. The operating system 1052 may include instructions for handling basic system services and for performing hardware dependent tasks. In some implementations, the operating system 1052 can be a kernel.

The memory 1050 can also store communication instructions 1054 to facilitate communicating with one or more additional devices, one or more computers and/or one or more servers, for example, to retrieve web resources from remote web servers. The memory 1050 can also include user interface instructions 1056, including graphical user interface instructions to facilitate graphic user interface processing.

Additionally, the memory 1050 can store sensor processing instructions 1058 to facilitate sensor-related processing and functions; telephony instructions 1060 to facilitate telephone-related processes and functions; messaging instructions 1062 to facilitate electronic-messaging related processes and functions; web browser instructions 1064 to facilitate web browsing-related processes and functions; media processing instructions 1066 to facilitate media processing-related processes and functions; location services instructions including GPS and/or navigation instructions 1068 and Wi-Fi based location instructions to facilitate location based functionality; camera instructions 1070 to facilitate camera-related processes and functions; and/or other software instructions 1072 to facilitate other processes and functions, e.g., security processes and functions, and processes and functions related to the systems. The memory 1050 may also store other software instructions such as web video instructions to facilitate web video-related processes and functions; and/or web shopping instructions to facilitate web shopping-related processes and functions. In some implementations, the media processing instructions 1066 are divided into audio processing instructions and video processing instructions to facilitate audio processing-related processes and functions and video processing-related processes and functions, respectively. A mobile equipment identifier, such as an International Mobile Equipment Identity (IMEI) 1074 or a similar hardware identifier can also be stored in memory 1050.

Each of the above identified instructions and applications can correspond to a set of instructions for performing one or more functions described above. These instructions need not be implemented as separate software programs, procedures, or modules. The memory 1050 can include additional instructions or fewer instructions. Furthermore, various functions may be implemented in hardware and/or in software, including in one or more signal processing and/or application specific integrated circuits.

Figure 11:
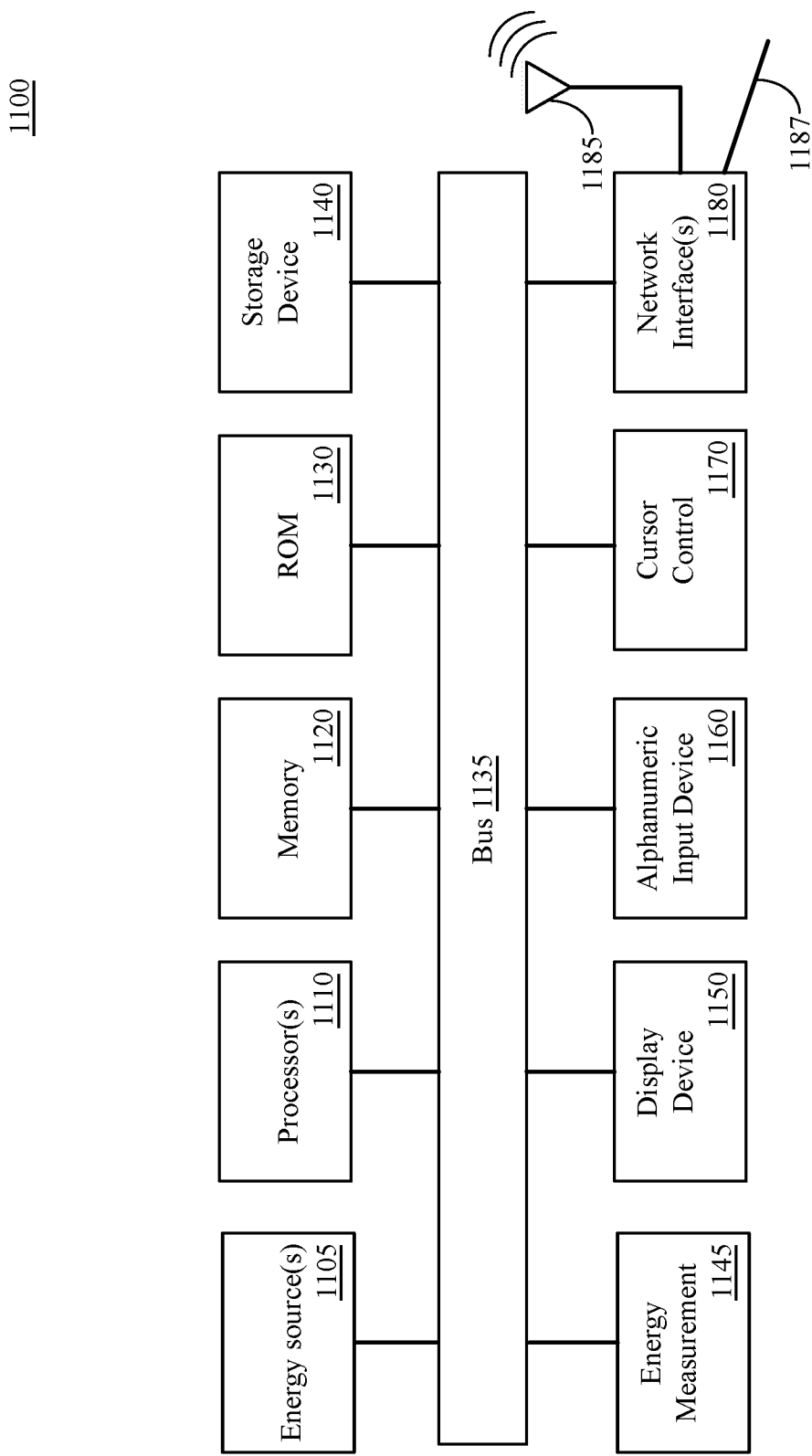
FIG. 11 is a block diagram of one embodiment of a computing system.

FIG. 11 is a block diagram of one embodiment of a computing system 1100. The computing system illustrated in FIG. 11 is intended to represent a range of computing systems (either wired or wireless) including, for example, desktop computer systems, laptop computer systems, tablet computer systems, cellular telephones, personal digital assistants (PDAs) including cellular-enabled PDAs, set top boxes, entertainment systems or other consumer electronic devices. Alternative computing systems may include more, fewer and/or different components. The computing system of FIG. 11 may be used to provide the computing device and/or the server device.

Computing system 1100 includes bus 1135 or other communication device to communicate information, and processor(s) 1110 coupled to bus 1135 that may process information.

While computing system 1100 is illustrated with a single processor, computing system 1100 may include multiple processors and/or co-processors 1110. Computing system 1100 further may include random access memory (RAM) or other dynamic storage device (e.g., main memory 1120), coupled to bus 1135 and may store information and instructions that may be executed by processor(s) 1110. Main memory 1120 may also be used to store temporary variables or other intermediate information during execution of instructions by processor(s) 1110.

Computing system 1100 may also include read only memory (ROM) 1130 and/or another data storage device 1140 coupled to bus 1135 that may store information and instructions for processor(s) 1110. Data storage device 1140 may be coupled to bus 1135 to store information and instructions. Data storage device 1140 such as flash memory or a magnetic disk or optical disc and corresponding drive may be coupled to computing system 1100.

Computing system 1100 may also be coupled via bus 1135 to display device 1150 to display information to a user. Computing system 1100 can also include an alphanumeric input device 1160, including alphanumeric and other keys, which may be coupled to bus 1135 to communicate information and command selections to processor(s) 1110. Another type of user input device is cursor control 1170, such as a touchpad, a mouse, a trackball, or cursor direction keys to communicate direction information and command selections to processor(s) 1110 and to control cursor movement on display device 1150. Computing system 1100 may also receive user input from a remote device that is communicatively coupled to computing system 1100 via one or more network interface(s) 1180.

Computing system 1100 further may include one or more network interface(s) 1180 to provide access to a network, such as a local area network. Network interface(s) 1180 may include, for example, a wireless network interface having antenna 1185, which may represent one or more antenna(e). Computing system 1100 can include multiple wireless network interfaces such as a combination of Wi-Fi, Bluetooth, near field communication (NFC), and/or cellular telephony interfaces. Network interface(s) 1180 may also include, for example, a wired network interface to communicate with remote devices via network cable 1187, which may be, for example, an Ethernet cable, a coaxial cable, a fiber optic cable, a serial cable, or a parallel cable.

In one embodiment, network interface(s) 1180 may provide access to a local area network, for example, by conforming to IEEE 802.11 b and/or IEEE 802.11 g standards, and/or the wireless network interface may provide access to a personal area network, for example, by conforming to Bluetooth standards. Other wireless network interfaces and/or protocols can also be supported. In addition to, or instead of, communication via wireless LAN standards, network interface(s) 1180 may provide wireless communications using, for example, Time Division, Multiple Access (TDMA) protocols, Global System for Mobile Communications (GSM) protocols, Code Division, Multiple Access (CDMA) protocols, Long Term Evolution (LTE) protocols, and/or any other type of wireless communications protocol.

Computing system 1100 can further include one or more energy sources 1105 and one or more energy measurement systems 1145. Energy sources 1105 can include an AC/DC adapter coupled to an external power source, one or more batteries, one or more charge storage devices, a USB charger, or other energy source. Energy measurement systems include at least one voltage or amperage measuring device that can measure energy consumed by the computing system 1100 during a predetermined period of time. Additionally, one or more energy measurement systems can be included that measure, e.g., energy consumed by a display device, cooling subsystem, Wi-Fi subsystem, or other frequently used or high-energy consumption subsystem.

Figure 12:
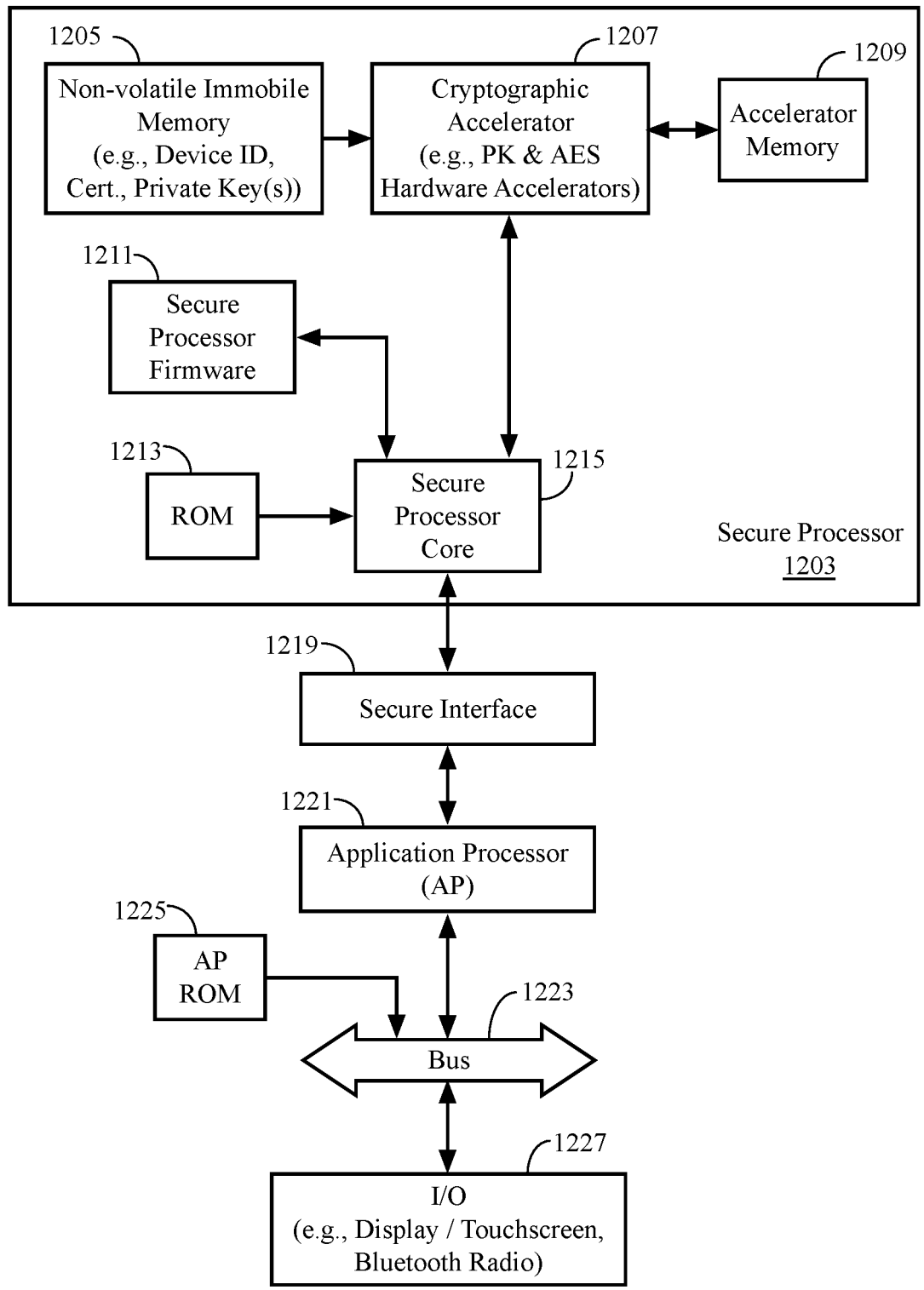
FIG. 12 illustrates a computing system including a secure processor.

FIG. 12 illustrates a computing system including a secure processor. In one embodiment the illustrated secure processor 1203 is a secure enclave processor, although other types of secure processors may be used to accelerate cryptographic operations described herein. The computing system 1200 can enable a device to perform secure accelerated cryptographic operations, to provide secure storage for a subset of private keys, and to enable the encryption of other private keys. A version of the computing system 1200 can be included in a primary device (e.g., smartphone) and a secondary device (e.g., computing device, wearable device, wireless accessory) as described herein. The computing system 1200 includes an application processor 1221 that is communicably coupled with a secure processor 1203 via a secure interface 1219. The computing system 1200 can be a portion of any of the client devices described herein. Additionally, the computing system 1200 can be included into one or more of the servers described herein. In one embodiment, the secure processor 1203 can be implemented as a system on chip. In another embodiment, the application processor 1221 and the secure processor 1203 can be implemented on a system on chip and include one or more processors and memory controllers and other components on a single integrated circuit. The secure processor 1203 can perform cryptographic operations as described herein, as well as other system security operations such as encrypting user files or verifying code signatures, processing user passcodes, or performing other security operations. The cryptographic operations can be performed in part by the secure processor core 1215 by executing software stored as firmware 1211 in the secure processor 1203. The secure processor core 1215 can also be coupled to a ROM 1213 which can be trusted software that can validate the software in the firmware 1211 before allowing that firmware to execute by checking a code signature of the firmware and verifying that the signature code indicates that the firmware is valid and has not been corrupted before allowing the firmware to be executed by the secure processor core 1215. The secure processor 1203 can also include a cryptographic accelerator such as cryptographic accelerator 1207 which can perform asymmetric cryptography as well as symmetric cryptography using a hardware accelerator. The cryptographic accelerator 1207 can be coupled to memory 1205, which may be non-volatile and immutable memory that can be used to store a device identifier or a set of device identifiers a secure manner. The memory 1205 can also be used to store a set of one or more certificates and private keys which are hidden from the rest of the system and are not readable by the rest of the system in one embodiment. The cryptographic accelerator 1207 has access to the private keys and other data within the memory 1205 and access to the memory 1205 is not allowed for components outside of the secure processor 1203. In one embodiment, the cryptographic accelerator 1207 can be coupled to an accelerator memory 1209 which can be a scratch pad memory used to perform the cryptographic operations that are performed by the cryptographic accelerator 1207. The application processor 1221 can be coupled to one or more buses 1223 which are coupled to one or more input and output (I/O) devices 1227, such as a touchscreen display a Bluetooth radio, an NFC radio, a Wi-Fi radio, etc. Other input and output devices can be included. The application processor 1221 is also coupled to an application processor ROM 1225, which provides software to boot the application processor. Similarly, the ROM 1213 provides code to boot the secure processor core 1215 within the secure processor 1203.

In the foregoing specification, the invention has been described with reference to specific embodiments thereof. It will, however, be evident that various modifications and changes can be made thereto without departing from the broader spirit and scope of the invention. The specification and drawings are, accordingly, to be regarded in an illustrative rather than a restrictive sense. The specifics in the descriptions and examples provided may be used anywhere in one or more embodiments. The various features of the different embodiments or examples may be variously combined with some features included and others excluded to suit a variety of different applications. Examples may include subject matter such as a method, means for performing acts of the method, at least one machine-readable medium including instructions that, when performed by a machine cause the machine to perform acts of the method, or of an apparatus or system according to embodiments and examples described herein. Additionally, various components described herein can be a means for performing the operations or functions described in accordance with an embodiment.

Embodiments described herein provide for a security model and interface for wearable device digital purposes. Embodiments enable a "thin" wearable device (e.g., a smart watch, smart glasses, bracelet, or the like) to be configured to be used as a primary device for making purchases of digital content, without reliance upon a companion electronic device, e.g., smartphone, computer, or the like.

One embodiment provides for a wearable device comprising a wireless network interface, a touch-sensitive display, a memory device to store instructions, and one or more processors to execute the instructions. The instructions cause the one or more processors to present, via the touch-sensitive display, a user interface to enable the wearable device to establish a communication connection with a server of a cloud service provider via the wireless network interface and transact a digital purchase from the server without assistance from a companion device.

One embodiment provides a non-transitory machine-readable medium storing instruction which, when executed by one or more processors of a wearable electronic device, cause the one or more processors to perform operations comprising presenting a request for a passcode used to unlock the wearable electronic device, receiving the passcode via the interface, using the passcode to unlock one or more keys that are securely stored on the wearable electronic device, establishing a communication connection with a server of a cloud service provider via a wireless network interface of the wearable device, and transacting a digital purchase from the server without assistance from a companion device, wherein the digital purchase is transacted at least in part using a signature generated with the one or more keys.

One embodiment provides for a data processing system on a wearable electronic device, the system comprising a wireless network interface, a touch-sensitive display, a memory device to store instructions, and one or more processors to execute the instructions. The instructions cause the one or more processors to present, via the touch-sensitive display, a user interface to enable the wearable device to present a request for a passcode used to unlock the wearable electronic device, receive the passcode via the interface, use the passcode to unlock one or more keys that are securely stored on the wearable electronic device, establish a communication connection with a server of a cloud service provider via the wireless network interface, and transact a digital purchase from the server without assistance from a companion device, wherein the digital purchase is transacted at least in part using a signature generated with the one or more keys.

One embodiment provides for a non-transitory machine-readable medium storing instructions to cause one or more processors to implement a provisioning process for a wearable device, the provisioning process comprising receiving a password equivalent token associated with a user of a wearable device, passing the password equivalent token to a password authentication process, receiving, from the password authentication process, a secure authentication token, passing the secure token and a public key generated by the wearable device to an identification settings process, receiving from the identification settings process an identification token uniquely associated with the wearable device, and storing the identification token in association with a public-private key pair for the wearable device in a secure memory location.

One embodiment provides for a method to implement a provisioning process for a wearable electronic device, where the method comprises receiving a password equivalent token associated with a user of a wearable device, passing the password equivalent token to a password authentication process, receiving, from the password authentication process, a secure authentication token, passing the secure token and a public key generated by the wearable device to an identification settings process, receiving, from the identification settings process, an identification token uniquely associated with the wearable device, and storing the identification token an a public-private key pair for the wearable device in a secure memory location.

One embodiment provides for a wearable electronic device comprising a wireless network interface, a touch-sensitive display, a memory device to store instructions, and one or more processors to execute the instructions, wherein the instructions cause the one or more processors to present, via the touch-sensitive display, a user interface to enable the wearable device to receive a password equivalent token associated with a user of a wearable device, pass the password equivalent token to a password authentication process, receive, from the password authentication process, a secure authentication token, pass the secure token and a public key generated by the wearable device to an identification settings process, receive, from the identification settings process, an identification token uniquely associated with the wearable device, and store the identification token in association with a public-private key pair for the wearable device in a secure memory location.

Other features of the present embodiments will be apparent from the accompanying drawings and from the detailed description above. Accordingly, the true scope of the embodiments will become apparent to the skilled practitioner upon a study of the drawings, specification, and following claims.

What is claimed is:

1. A non-transitory machine-readable medium storing instruction which, when executed by one or more processors of a wearable electronic device, cause the one or more processors to perform operations comprising:
presenting a request for a passcode used to unlock the wearable electronic device;
receiving the passcode via a user interface presented by the wearable electronic device;
using the passcode to unlock one or more keys that are securely stored on the wearable electronic device;
establishing a communication connection with a server of a cloud service provider via a wireless network interface of the wearable electronic device; and
transacting a digital purchase from the server without assistance from a companion device, wherein the digital purchase is transacted at least in part using a signature generated with the one or more keys.

2. The non-transitory machine-readable medium as in claim 1, wherein the wearable electronic device comprises at least one sensor to detect a physical input from a user of the wearable electronic device.

3. The non-transitory machine-readable medium as in claim 2, the operations additionally comprising presenting an interface via a touch-sensitive display, the interface to present a request for a physical input as validation of a request to transact the digital purchase.

4. The non-transitory machine-readable medium as in claim 1, wherein one or more keys are stored in a secure memory of a secure processor of the wearable electronic device.

5. The non-transitory machine-readable medium as in claim 1, wherein the wearable electronic device includes a heart monitor, health sensor, glucose monitor, GPS tracker, or fitness tracker.

6. The non-transitory machine-readable medium as in claim 5, wherein the wearable electronic device includes a smartwatch device, a virtual reality or augmented reality head mounted display, jewelry, shoes, clothes, or other wearable item.

7. A wearable electronic device, comprising:
a wireless network interface;
a touch-sensitive display;
a memory device to store instructions; and
one or more processors to execute the instructions, wherein the instructions cause the one or more processors to present, via the touch-sensitive display, a user interface to enable the wearable electronic device to:
present a request for a passcode used to unlock the wearable electronic device;
receive the passcode via the user interface;
use the passcode to unlock one or more keys that are securely stored on the wearable electronic device
establish a communication connection with a server of a cloud service provider via the wireless network interface; and
transact a digital purchase from the server without assistance from a companion device, wherein the digital purchase is transacted at least in part using a signature generated with the one or more keys.

8. The wearable device as in claim 7, wherein the one or more processors are to present an interface via the touch-sensitive display to:
enable a user to browse media items available for acquisition from a media store accessible via the wireless network interface;
receive a selection of an item presented via the interface; and
transact the digital purchase from the server to acquire the item selected via the interface.

9. The wearable device as in claim 7, wherein the wearable electronic device comprises at least one sensor to detect a physical input from a user of the wearable electronic device.

10. The wearable device as in claim 7, the one or more processors to present an interface via the touch-sensitive display, the interface to present a request for a physical input as validation of a request to transact the digital purchase.

11. The wearable device as in claim 7, wherein the one or more keys are stored in a secure memory of a secure processor of the wearable electronic device.

12. The wearable device as in claim 7, wherein the wearable electronic device additionally includes a heart monitor, health sensor, glucose monitor, GPS tracker, or fitness tracker.

13. The wearable device as in claim 12, wherein the wearable electronic device includes a smartwatch device, a virtual reality or augmented reality head mounted display, jewelry, shoes, clothes, or other wearable item.

14. A method executed by one or more processors of a wearable electronic device, the method comprising:
presenting a request for a passcode used to unlock the wearable electronic device;
receiving the passcode via a user interface presented by the wearable electronic device;
using the passcode to unlock one or more keys that are securely stored on the wearable electronic device;

establishing a communication connection with a server of a cloud service provider via a wireless network interface of the wearable electronic device; and transacting a digital purchase from the server without assistance from a companion device, wherein the digital purchase is transacted at least in part using a signature generated with the one or more keys.

15. The method according to claim 14, wherein the wearable electronic device comprises at least one sensor to detect a physical input from a user of the wearable electronic device.

16. The method according to claim 15, wherein the wearable electronic device comprises a secure memory to store a public/private key pair, wherein the secure memory is included within a secure processor of the wearable electronic device.

17. The method according to claim 14, wherein the one or more processors are additionally to present the user interface via a touch-sensitive display to present a request for a physical input as validation of a request to transact the digital purchase.

18. The method according to claim 14, wherein the wearable electronic device additionally includes a heart monitor, health sensor, glucose monitor, GPS tracker, or fitness tracker.

19. The method according to claim 18, wherein the wearable electronic device includes a smartwatch device, a virtual reality or augmented reality head mounted display, jewelry, shoes, clothes, or other wearable item.

20. The method according to claim 14, further comprising:

enabling a user to browse media items available for acquisition from a media store accessible via the wireless network interface;

receiving a selection of an item presented via the interface; and transacting the digital purchase from the server to acquire the item selected via the user interface.

* * * * *